(12) United States Patent
Zwirko et al.

(10) Patent No.: US 10,894,979 B2
(45) Date of Patent: Jan. 19, 2021

(54) CONSTRUCTION OF NEXT GENERATION SEQUENCING (NGS) LIBRARIES USING COMPETITIVE STRAND DISPLACEMENT

(71) Applicant: INTEGRATED DNA TECHNOLOGIES, INC., Coralville, IA (US)

(72) Inventors: Zachary Zwirko, Redwood City, CA (US); Yu Zheng, Redwood City, CA (US); Mirna Jarosz, Mountain View, CA (US); Caifu Chen, Palo Alto, CA (US); Joseph Walder, Chicago, IL (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 105 days.

(21) Appl. No.: 16/138,845

(22) Filed: Sep. 21, 2018

(65) Prior Publication Data
US 2019/0010540 A1    Jan. 10, 2019

Related U.S. Application Data

(63) Continuation-in-part of application No. 15/880,762, filed on Jan. 26, 2018, and a continuation-in-part of application No. PCT/US2018/015391, filed on Jan. 26, 2018.

(60) Provisional application No. 62/451,267, filed on Jan. 27, 2017, provisional application No. 62/562,739, filed on Sep. 25, 2017, provisional application No. 62/451,267, filed on Jan. 27, 2017.

(51) Int. Cl.
| | | |
|---|---|---|
| *C12Q 1/6855* | (2018.01) | |
| *C12Q 1/6806* | (2018.01) | |
| *C12Q 1/6869* | (2018.01) | |
| *C40B 80/00* | (2006.01) | |
| *C40B 40/06* | (2006.01) | |
| *C12N 15/10* | (2006.01) | |
| *C40B 20/04* | (2006.01) | |

(52) U.S. Cl.
CPC ....... *C12Q 1/6855* (2013.01); *C12N 15/1093* (2013.01); *C12Q 1/6806* (2013.01); *C40B 40/06* (2013.01); *C12Q 1/6869* (2013.01); *C40B 20/04* (2013.01); *C40B 80/00* (2013.01)

(58) Field of Classification Search
None
See application file for complete search history.

(56) References Cited

U.S. PATENT DOCUMENTS

| | | |
|---|---|---|
| 2007/0128624 A1 | 6/2007 | Gormley et al. |
| 2011/0104785 A1 | 5/2011 | Vaidyanathan et al. |
| 2013/0203123 A1 | 8/2013 | Nelson et al. |
| 2014/0357528 A1 | 12/2014 | Robb et al. |
| 2015/0099671 A1 | 4/2015 | Moore et al. |
| 2016/0376647 A1 | 12/2016 | Travers et al. |
| 2017/0226498 A1 | 8/2017 | Zheng et al. |

FOREIGN PATENT DOCUMENTS

| | | | |
|---|---|---|---|
| JP | 2016-514460 A | 5/2016 | |
| WO | 2015/117040 A1 | 8/2015 | |
| WO | 2015/134552 A1 | 9/2015 | |
| WO | WO-2015134552 A1 * | 9/2015 | ....... C12Q 2521/525 |
| WO | 2016/133764 A1 | 8/2016 | |
| WO | 2017/139260 A1 | 8/2017 | |

OTHER PUBLICATIONS

International Search Report and Written Opinion for Application No. PCT/US2018/015391 dated May 23, 2018 (8 pages).
Rossi et al., "Fuctional characterization of the T4 DNA ligase: a new insight into the mechanism of action," Nucleic Acids Research, 1997, 25(11): 2106-2113.
Liu et al., "DNA ligases ensure fidelity by interrogating minor groove contacts," Nucleic Acids Research, 2004, 32(15): 4503-4511.
Lohman et al., "DNA Ligases," Curr. Protoc. Mol. Biol., 2011, 94:3.14.1-3.14.7.
United States Patent Office Action for U.S. Appl. No. 15/880,762 dated Oct. 31, 2019 (10 pages).
United States Patent Office Notice of Allowance for U.S. Appl. No. 15/880,762 dated Feb. 20, 2020 (7 pages).
Australian Patent Office Examination Report No. 1 for Application No. 2018212756 dated Jun. 16, 2020 (4 pages).
Japanese Patent Office Action for Application No. 2019-541148 dated Jul. 13, 2020 (10 pages, English translation included).
European Patent Office Extended Search Report for Application No. 18745378.2 dated Sep. 29, 2020 (6 pages).
Canadian Patent Office Action for Application No. 3,046,617 dated Oct. 14, 2020 (3 pages).

* cited by examiner

*Primary Examiner* — Kaijiang Zhang
(74) *Attorney, Agent, or Firm* — Michael Best & Friedrich LLP

(57) ABSTRACT

The invention pertains to construction of next-generation DNA sequencing (NGS) libraries for whole genome sequencing, targeted resequencing, sequencing-based screening assays, metagenomics, or any other application requiring sample preparation for NGS.

8 Claims, 35 Drawing Sheets

Specification includes a Sequence Listing.

| Input | Replicates | PCR Cycles | # of reads | % duplication | | Sequence Data |
|---|---|---|---|---|---|---|
| | | | | LOTUS | Kapa | |
| 25 ng | 3 | 10 | 16M | 78% | 87% | |
| 50 ng | 3 | 9 | 36M | 82% | 87% | SID285 |
| 100 ng | 3 | 8 | 60M | 83% | 90% | |
| 250 ng | 3 | 7 | 14M | 46% | 57% | |

FIG. 11

| Input | Replicates | PCR Cycles | # of reads | % duplication | | Sequence Data |
|---|---|---|---|---|---|---|
| | | | | LOTUS | Kapa | |
| 1 ng | 3 | 12 | 12M | 95% | 97% | |
| 10 ng | 3 | 10 | 28M | 83% | 95% | SID285 |
| 25 ng | 3 | 8 | 90M | 96% | 97% | |

FIG. 15

CONSTRUCTION OF NEXT GENERATION SEQUENCING (NGS) LIBRARIES USING COMPETITIVE STRAND DISPLACEMENT

CROSS-REFERENCE TO RELATED APPLICATION(S)

The present application is a continuation-in-part of U.S. patent application Ser. No. 15/880,762, filed on Jan. 26, 2018, which claims priority to U.S. Provisional Patent Application No. 62/451,267, filed on Jan. 27, 2017, the entire contents of each of which are fully incorporated herein by reference. The present application also claims priority to U.S. Provisional Patent Application No. 62/562,739, filed on Sep. 25, 2017, and International Patent Application No. PCT/US2018/015391, filed on Jan. 26, 2018, which claims priority to U.S. Provisional Patent Application No. 62/451,267, filed on Jan. 27, 2017, the entire contents of each of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 31,507 Byte ASCII (Text) file named "013670-9051-US04-SEQ-LIST-09-21-18.txt" created on Sep. 21, 2018.

TECHNICAL FIELD

The disclosure relates the construction of next-generation DNA sequencing (NGS) libraries. Specifically, the disclosure relates to sequencing adapters and methods for the construction of NGS libraries.

BACKGROUND

Next Generation Sequencing (NGS) has evolved into a very powerful tool in molecular biology, allowing for the rapid progress in fields such as genomic identification, genetic testing, drug discovery, and disease diagnosis. As this technology continues to advance, the volume of nucleic acids that can be sequenced at one time is increasing. This allows researchers to sequence larger samples, as well as to increase the number of reads per sample, enabling the detection of small sequence variations within that sample.

As the volume and complexity of NGS processing increases, so does the rate of experimental error. While much of this error occurs in the sequencing and processing steps, errors can also occur during the sample preparation steps. This is particularly true during the conversion of the sample into a readable NGS library by which adapter sequences are attached to the ends of each fragment of a fragmented sample (library fragment) in a uniform fashion.

There are several types of errors that can occur during the execution of next generation sequencing (NGS), and it is important to be able to differentiate between true rare variants, such as rare alleles or mutations that exist in the patient, and errors that arise from sequencing and/or sample preparation. Particularly problematic are errors that are introduced during library construction, prior to library amplification via polymerase chain reaction (PCR). Such errors can propagate during PCR, leading to multiple copies of sequences containing the error, making it difficult to distinguish between the errors and true variants.

Accordingly, what is needed are methods for construction of NGS libraries that minimize errors during library construction.

SUMMARY

The disclosure relates to sequencing adapters and methods for the construction of next-generation DNA sequencing (NGS) libraries for whole genome sequencing, targeted resequencing, sequencing-based screening assays, metagenomics, or any other application requiring sample preparation for NGS. The disclosed methods consist of a two-step ligation process by which a first sequencing adapter is ligated to end repaired DNA fragments via blunt end ligation and a second sequencing adapter is then ligated to the first ligation product via splint end ligation.

Other aspects of the disclosure will become apparent by consideration of the detailed description and accompanying drawings.

BRIEF DESCRIPTION OF THE DRAWINGS

FIG. 11 is a table showing library preparation at four different input concentrations of FFPE DNA and the final duplication percentage of the sequenced library. The FIG. compares the duplication percentage of the CSD (LOTUS) prepared library to KAPA's library preparation method.

FIG. 15 is a table showing library preparation at 3 different input concentrations of cell free DNA (cfDNA) and the final duplication percentage of the sequence library. Three input concentrations of 1 ng, 10 ng, and 25 ng were prepared with 3 replicates of each concentration.

DETAILED DESCRIPTION

I. Definitions

Figure 1:
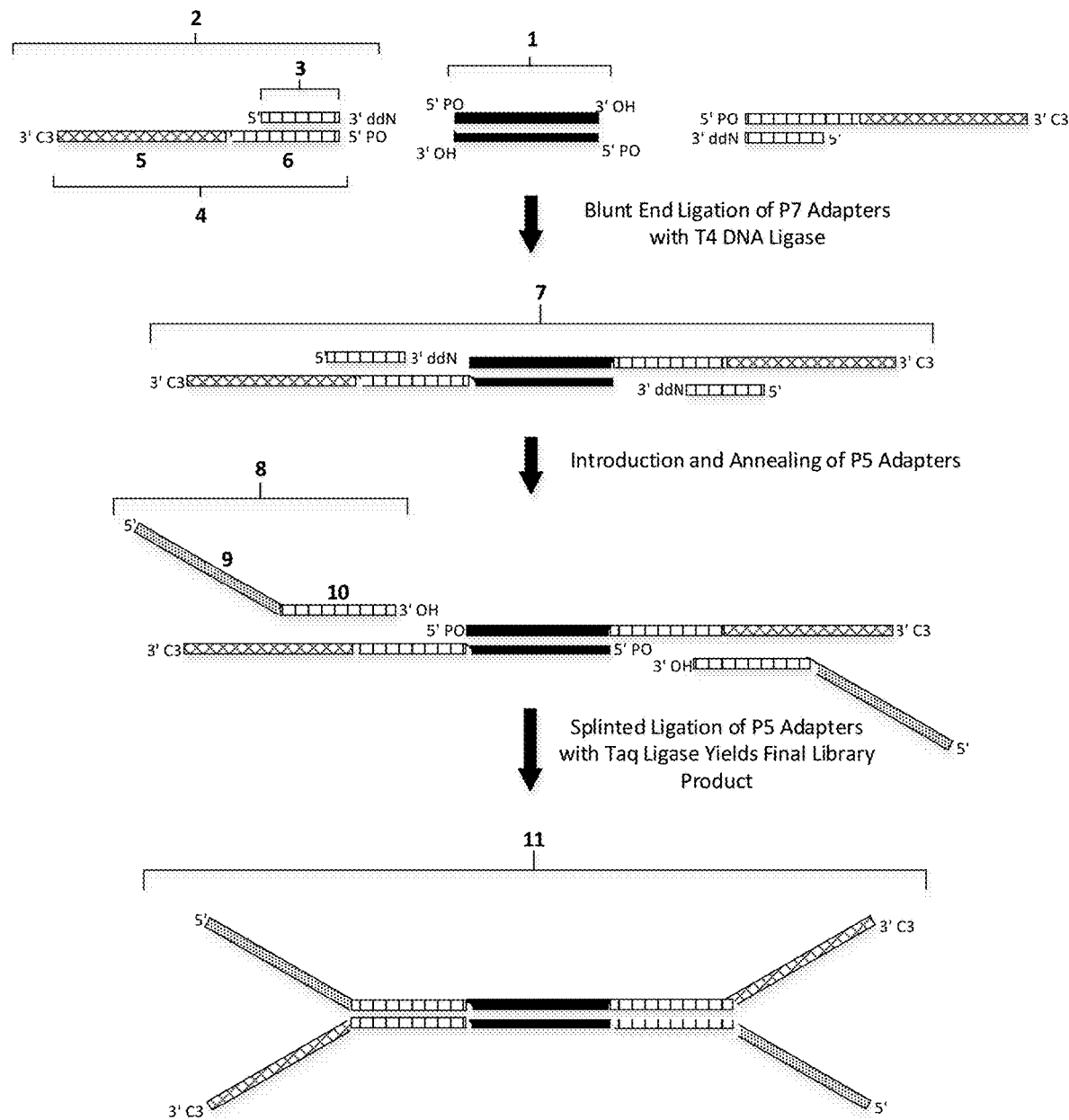
FIG. 1 is a schematic demonstrating an exemplary embodiment of the Competitive Strand Displacement (CSD) method. The first step consists of the attachment of a first sequencing adapter (2) to the DNA target fragment (1) via blunt end ligation catalyzed by T4 DNA ligase. Said first sequencing adapter consists of a first and second DNA strand. The first DNA strand (4) has a C3 blocking group on its 3' end, a phosphate group on its 5' end (5' PO), and consists of a first sequence (6) which is complementary to, but longer than, the second DNA strand (3) and a second, non-complementary tag sequence (5) that contains the first sequencing primer binding site and, optionally, a UMI and/or sample barcode sequence. The second DNA strand (3) is a truncated oligonucleotide, with a dideoxy nucleotide base (ddN) at its 3' end, and serves to facilitate the blunt end ligation of the 5' PO of the second DNA strand to the 3' OH of the target fragment, leading to the first ligation product (7). The second step consists of the attachment of a second sequencing adapter (8) to the first ligation product (7) via splint end ligation catalyzed by Taq ligase. Said second sequencing adapter has a 3' OH and consists of a first sequence (10) that is complimentary to the first sequence (6) of the first sequencing adapter and a second sequence (9) that contains the second sequencing primer binding site and, optionally, a second UMI and/or sample barcode sequence. Since the length of the complementary sequence of the second adapter (10) is longer than that of the truncated oligo of the first adapter (3), the second adapter is able to displace the truncated oligo during the annealing step that precedes the splint end ligation. The splint end ligation leads to the final library product (11).

Unless otherwise defined, all technical and scientific terms used herein have the same meaning as commonly understood by one of ordinary skill in the art. In case of conflict, the present document, including definitions, will control. Example methods and materials are described below, although methods and materials similar or equivalent to those described herein can be used in practice or testing of the present disclosure. The materials, methods, and examples disclosed herein are illustrative only and not intended to be limiting.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The terms "adapter", "sequencing adapter", "adaptor", and "sequencing adaptor" as used interchangeably herein refer to single stranded or double stranded oligonucleotides that can be ligated to the ends of other DNA or RNA molecules.

The terms "adenylated", or "pre-adenylated", as used herein, refer to a state by which a strand of DNA has an adenosine 5'-monophosphate (AMP) covalently attached to its 5'-terminal phosphate via a pyrophosphate bond. The terms "adenylate", or "adenylation", as used herein, refer to the process of covalently attaching an AMP either to a protein side chain or to the 5'-terminal phosphate of a DNA strand. The term "adenyl group", as used herein, refers to an AMP that is either covalently attached to, or transferred between, a protein sidechain and/or DNA strand.

The term "consensus sequence", as used herein, refers to a sequence obtained by comparing multiple sequences within a family of sequences. Sequence variations that are present in some, but not in the majority of sequences, in the family may be designated as errors and subsequently removed from the analysis. On the other hand, sequence variations that are present in the majority of sequences within a family may be designated as true variants that were present in the original genetic material being analyzed. The term "consensus calling", as used herein, refers to the process to determining if a genetic variation is a true variation or an error.

The term "deduplication", or "dedup", as used herein, refers to the removal of reads that are determined to be duplicates, from the analysis. Reads are determined to be duplicates if they share the same start stop sites and/or UMI sequences. One purpose of deduplication is to create a consensus sequence whereby those duplicates that contain errors are removed from the analysis. Another purpose of deduplication is to estimate the complexity of the library. A library's "complexity", or "size", as used herein, refers to the number of individual sequence reads that represent unique, original fragments and that map to the sequence being analyzed.

The terms "depth of coverage", "coverage depth" or "target coverage", as used herein, refer to the number of sequenced DNA fragments (i.e., a reads) that map to a genomic target. The deeper the coverage of a target region (i.e., the more times the region is sequenced), the greater the reliability and sensitivity of the sequencing assay. In general, a coverage depth of 500-1000×, or higher, is often required for the detection of low frequency sequence variations.

The term "family", as used herein, refers to a group of reads that are determined to be duplicates based on their having the same start stop sites and/or UMIs. In variant calling, large families with multiple clones are desirable since they can be used to build stronger consensus sequences than those with only a few clones to compare. For very small family sizes with one or two clones, a consensus cannot be called, resulting in potentially important data being thrown out.

The terms "fragments", "target fragments", or "inserts", as used herein, refer to fragments of DNA, created from the fragmentation of a DNA sample, which are processed into an NGS library and sequenced. The processing of these fragments usually involves end repair and A-tailing, followed by the addition of sequencing adapters and amplification.

"PPV", or Positive Predictive Value, is the probability that a sequence called as unique is actually unique. PPV=true positive/(true positive+false positive). "Sensitivity" is the probability that a sequence that is unique will be called as unique. Sensitivity=true positive/(true positive+false negative).

The terms "start stop sites", or "fragment ends", as used herein, refer to the sequences at the 5' and 3' ends of a sheared library fragment that become directly ligated to the sequencing adapters. Start stop sites can be used to determine if two similar sequences are derived from separate molecules or are cloned copies of the same original fragment. In order for different original fragments to have the same start stop sites, the shearing events that created them would have had to cleave at exactly the same sites, which has a low probability. Clones, on the other hand, should always have the same start stop sites. As such, any fragments that share the same start stop site (due to random shearing), are usually considered duplicates. The term "position-based", as used herein, refers to the use of stop start sites as a criterion for determining whether or not a read is a duplicate of another.

A "start stop collision", as defined herein, is the occurrence of multiple unique fragments that contain the same start stop sites. Due to the rarity of start stop collisions, they are usually only observed when either performing ultra deep sequencing with a very high number of reads, such as when performing low variant detection, or when working with DNA samples that have a small size distribution, such as plasma DNA. As such, start stop sites may not be enough in those scenarios since one would run the risk erroneously removing unique fragments, mistaken as duplicates, during the deduplication step. In these cases, the incorporation of UMIs into the workflow can potentially rescue a lot of complexity.

The term "UMI", or "Unique Molecular Identifier", as used herein, refers to a tag, consisting of a sequence of degenerate or varying bases, which is used to label original molecules in a sheared nucleic acid sample. In theory, due to the extremely large number of different UMI sequences that can be generated, no two original fragments should have the same UMI sequence. As such, UMIs can be used to determine if two similar sequence reads are each derived from a different, original fragment or if they are simply duplicates, created during PCR amplification of the library, which were derived from the same original fragment.

UMIs are especially useful, when used in combination with start stop sites, for consensus calling of rare sequence variants. For example, if two fragments have the same start and stop site but have a different UMI sequences, what would otherwise have been considered two clones arising from the same original fragment could now be properly designated as unique molecules. As such, the use of UMIs combined with start stop sites often leads to a jump in the coverage number since unique fragments that would have been labeled as duplicates using start stop sites alone will be labelled as unique from each other due to them having different UMIs. It also helps improve the Positive Predictive Value ("PPV") by removing false positives. There is currently a lot of demand for UMIs, as there are some rare variants that can only be found via consensus calling using UMIs.

The term "variant calling", as used herein, refers to the process of determining if a sequence variation is a true variant derived from the original sample, and thus used in the analysis, or the result of a processing error and thrown out.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. For example, when a pressure range is described as being between ambient pressure and another pressure, a pressure that is ambient pressure is expressly contemplated.

II. Sequencing Adapters

Disclosed herein are sequencing adapters. The sequencing adapters may be used in the methods for NGS library preparation disclosed herein. The sequencing adapters comprise a first DNA strand and a second DNA strand. The first DNA strand has a blocking group at the 3' end and a 5' phosphate. The blocking group may be a C3 spacer. The first DNA strand may contain a first sequencing primer binding site. The first DNA strand may contain a unique molecular identifier. The first DNA strand may be selected from the group comprising SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, or SEQ ID NO: 33.

The second DNA strand has a dideoxy nucleotide base (ddN) at the 3' end. The second DNA strand may be partially complementary to the first DNA strand. The dideoxy nucleotide base can be a ddA, ddT, ddC, or ddG. The second DNA strand may contain a unique molecular identifier. The second DNA strand can be from 5 to 15 bases in length. For example, the second DNA strand can be 5 bases, 6 bases, 7 bases, 8 bases, 9 bases, 10 bases, 11 bases, 12 bases, 13 bases, 14 bases, or 15 bases in length. In some embodiments, the second DNA strand is 10 bases. The second DNA strand may be selected from the group comprising SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO:42, SEQ ID NO: 43, SEQ ID NO: 44, SEQ ID NO: 45, SEQ ID NO: 46, SEQ ID NO: 47, SEQ ID NO: 48, or SEQ ID NO: 49.

III. Methods for NGS Library Construction

Provided herein are high throughput methods for NGS library construction. The methods described herein are based on novel adapter ligation strategies that can minimize the formations of both fragment chimeras and adapter dimers and accurately convert DNA samples into sequencing libraries in under a day. The disclosed methods for NGS library preparation are referred to herein as Competitive Strand Displacement (CSD) methods.

The general strategy used to overcome errors that propagate during PCR is referred to as consensus calling, whereby sequence reads that are PCR copies of a single, original fragment are grouped together and compared to similar groups of copies, derived from other original fragments, which overlap in sequence. If a variation is present in one group of clones and not the others then it is most likely an error propagated by PCR, whereas variations present in several groups are most likely true variants. In order to perform this analysis one must be able to differentiate between clones derived from one molecule and those derived from another.

Two errors that occur during library construction, and which are reduced by the methods described herein, are the formation of (1) fragment chimeras and (2) adapter dimers.

Fragment chimeras are the result of library fragments ligating with one another without the adapter sequences, resulting in longer fragments that contain unrelated sequences juxtaposed to one another. These unrelated sequences would thus be mistakenly read as a continuous sequence. As such, suppression of fragment chimera formation during library construction is important for reducing downstream sequencing errors.

Adapter dimers are the result of self-ligation of the adapters without a library insert sequence. These dimers form clusters very efficiently, reduce reaction efficiencies, and consume valuable space on the flow cell. This is especially problematic when dealing with ultra-low DNA input quantities in the picogram range. At such low DNA input levels, adapter dimers can constitute a majority of the NGS library molecules formed, thus reducing the amount of useful information generated by DNA sequencing. For this reason, suppression of adapter dimer formation during library construction is a challenging task.

The CSD methods described herein are exemplified by several embodiments, described in more detail below. The embodiments are intended to exemplify, not limit, the scope of the disclosure.

In a first embodiment of the CSD method (FIG. 1), fragmented DNA is subjected to an end-repair reaction producing blunt 5' phosphorylated inserts with free 3' OH ends. This may be accomplished with T4 Polynucleotide Kinase (PNK) and T4 DNA polymerase, or any other combination of enzymes that leaves blunt ends with 5' phosphates and 3' hydroxyl groups. Following end-repair, the first sequencing adapter (P5 or P7 for Illumina platforms) is attached to the 3' end of insert DNA via blunt ligation using T4 DNA ligase; one strand of the adapter is 5' phosphorylated to facilitate ligation, while the complementary strand is blocked on the 3' end with a dideoxy nucleotide (ddN) to prevent ligation. The second sequencing adapter is then attached to the 5' ends of biological inserts through a splinted ligation reaction linking the 3' ends of adapter molecules to the phosphorylated 5' ends of the inserts. This ligation can be performed using Taq DNA ligase, or any other ligase capable of performing splinted ligations with little activity on blunt-ended substrates (Ampligase, 9° N, Tth, etc.). Since these ligases prefer splinted ligation, adapter dimers are minimized, which mitigates the need for size-selection post-ligation. Following the second ligation, the newly constructed library molecules can either be sequenced directly ("PCR-free") or amplified via PCR prior to sequencing. Representative examples of the first and second strands of the first sequencing adapter for the first embodiment are provided as SEQ ID NOs:3-10, and SEQ ID NO:17, respectively. Representative examples of the second sequencing adapter for the first embodiment are provided as SEQ ID NOs:1-2. All representative examples for the first embodiment are offered to illustrate, but not to limit, the claimed method.

Figure 2:
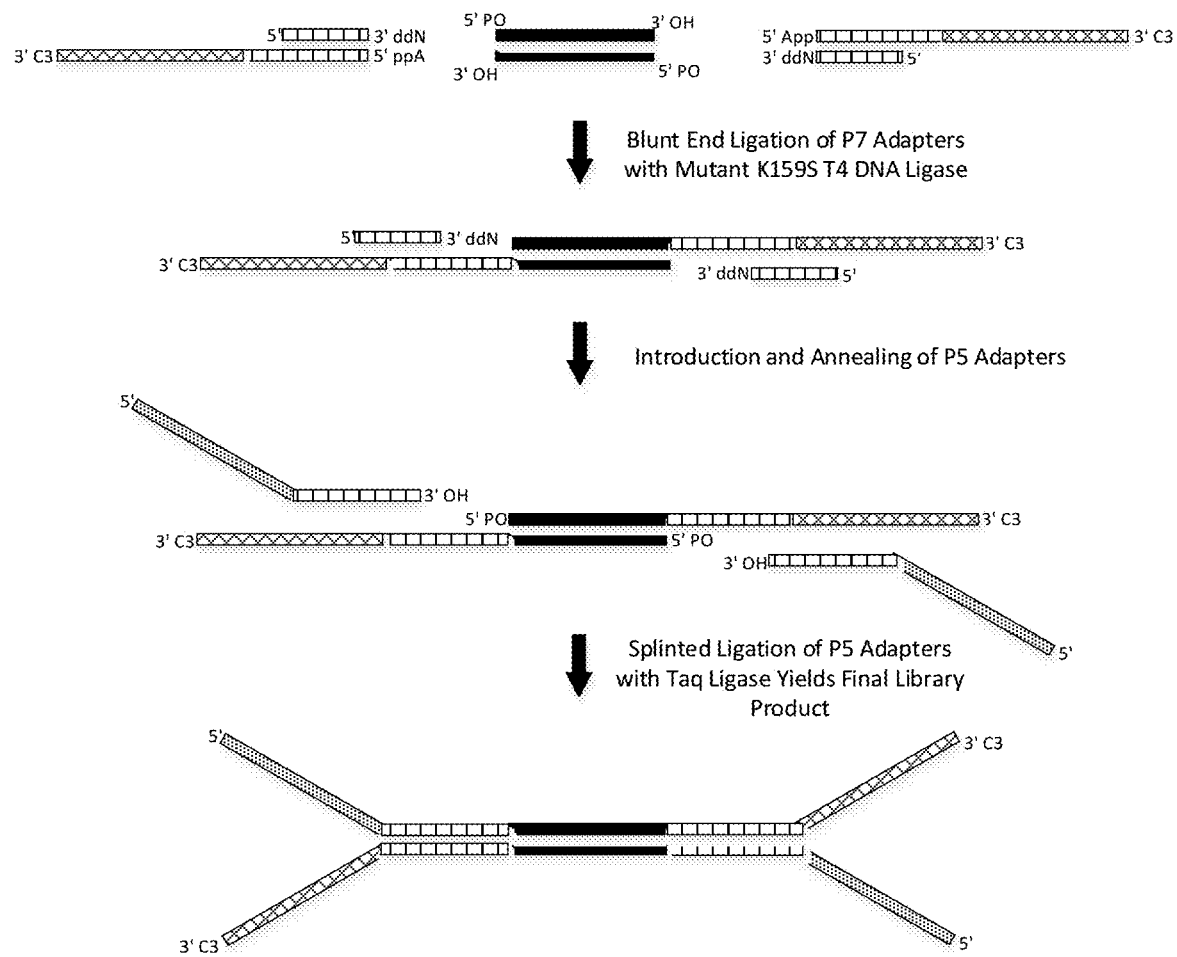
FIG. 2 is a schematic demonstrating an exemplary embodiment of the CSD method. The elements of the second embodiment are similar to those of the first embodiment, the difference being that the first sequencing adapter is pre-adenylated at the 5' end (5' ppA) of the first strand and that the blunt end ligation is catalyzed by a mutant T4 DNA ligase, K159S, that cannot use ATP as a substrate for ligation and can thus only ligate the pre-adenylated strand of the first adapter to the 3' OH of the target fragment.

In a second embodiment of the CSD method, a mutant T4 DNA ligase, K159S (see U.S. application Ser. No. 15/426, 543, referenced in its entirety), is used for the first ligation (FIG. 2) This mutant cannot utilize ATP to adenylate substrates prior to ligation, and is thus only capable of ligating substrates that were pre-adenylated. This feature can be exploited by performing ligation with pre-adenylated sequencing adapters as this will only result in adapter-to-insert ligation events (rather than insert-to-insert), which greatly suppresses chimera formation. Furthermore, the ligation efficiency of wild-type T4 DNA ligase is thought be hindered by "aborted ligation" events where adenylated ligase units transfer adenyl groups to inserts, but fail to effectively join 5' and 3' ends. In such instances, ligase units will be quickly re-adenylated rendering them inactive on DNA that has already been adenylated. Since the mutant cannot be adenylated, aborted ligation events are not problematic and ligation efficiency is increased relative to that of wild-type T4 DNA ligase. Representative examples of the first sequencing adapter for the second embodiment are provided as SEQ ID NOs:11-16. All representative examples for the second embodiment are offered to illustrate, but not to limit, the claimed method.

Figure 3:
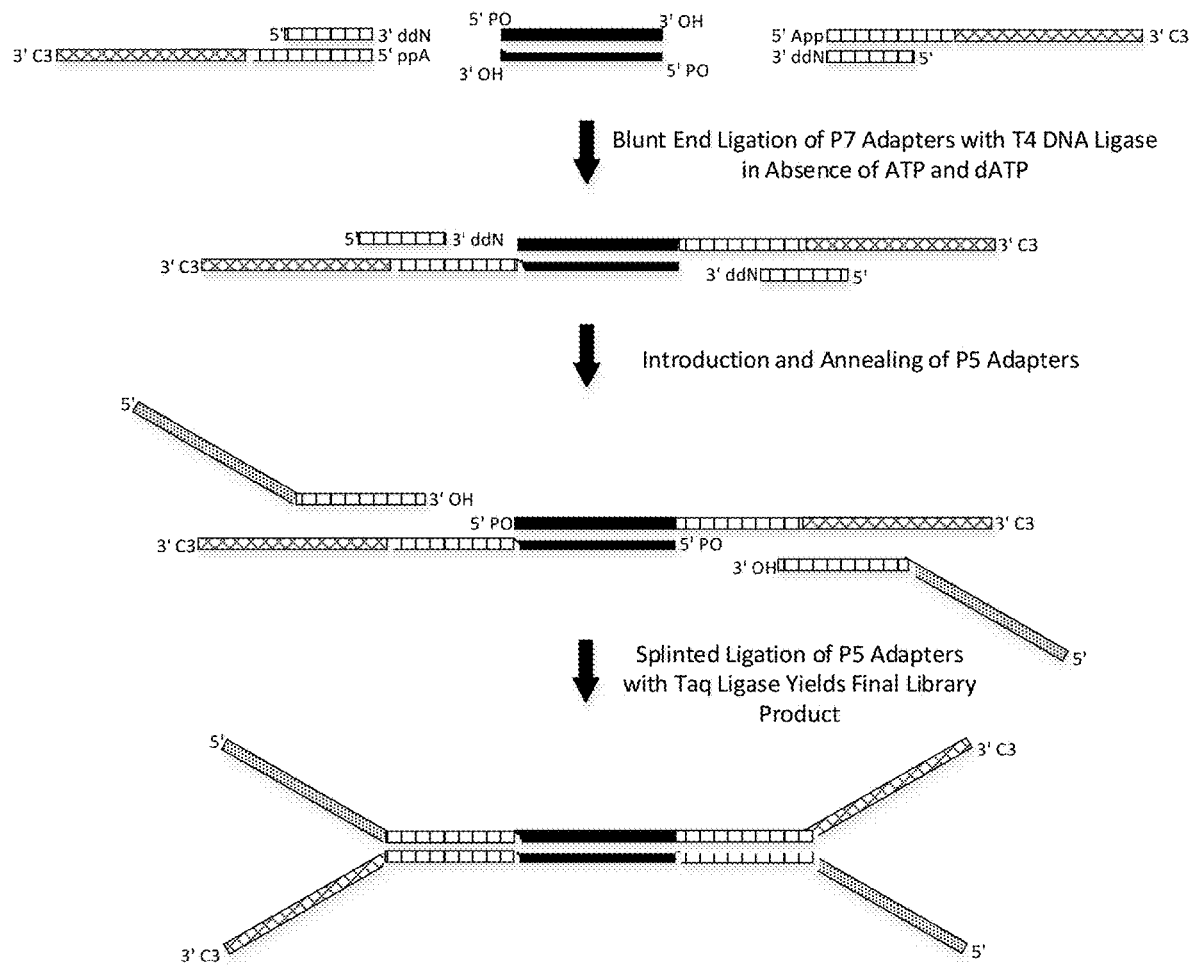
FIG. 3 is a schematic demonstrating an exemplary embodiment CSD method. The elements of the third embodiment are similar to those of the second embodiment, the difference being that the blunt end ligation is catalyzed by wildtype T4 DNA ligase in the absence of ATP. Since ATP is unavailable as a substrate for ligation, the wildtype T4 DNA ligase can thus only ligate the pre-adenylated strand of the first adapter to the 3' OH of the target fragment.

In a third embodiment of the CSD method, the pre-adenylated adapters in the first ligation step are ligated onto the 3' ends of the target fragments via a wild type T4 ligase, instead of the K159S mutant, and in the absence of ATP, thus preventing the formation of fragment chimeras (FIG. 3).

Figure 4:
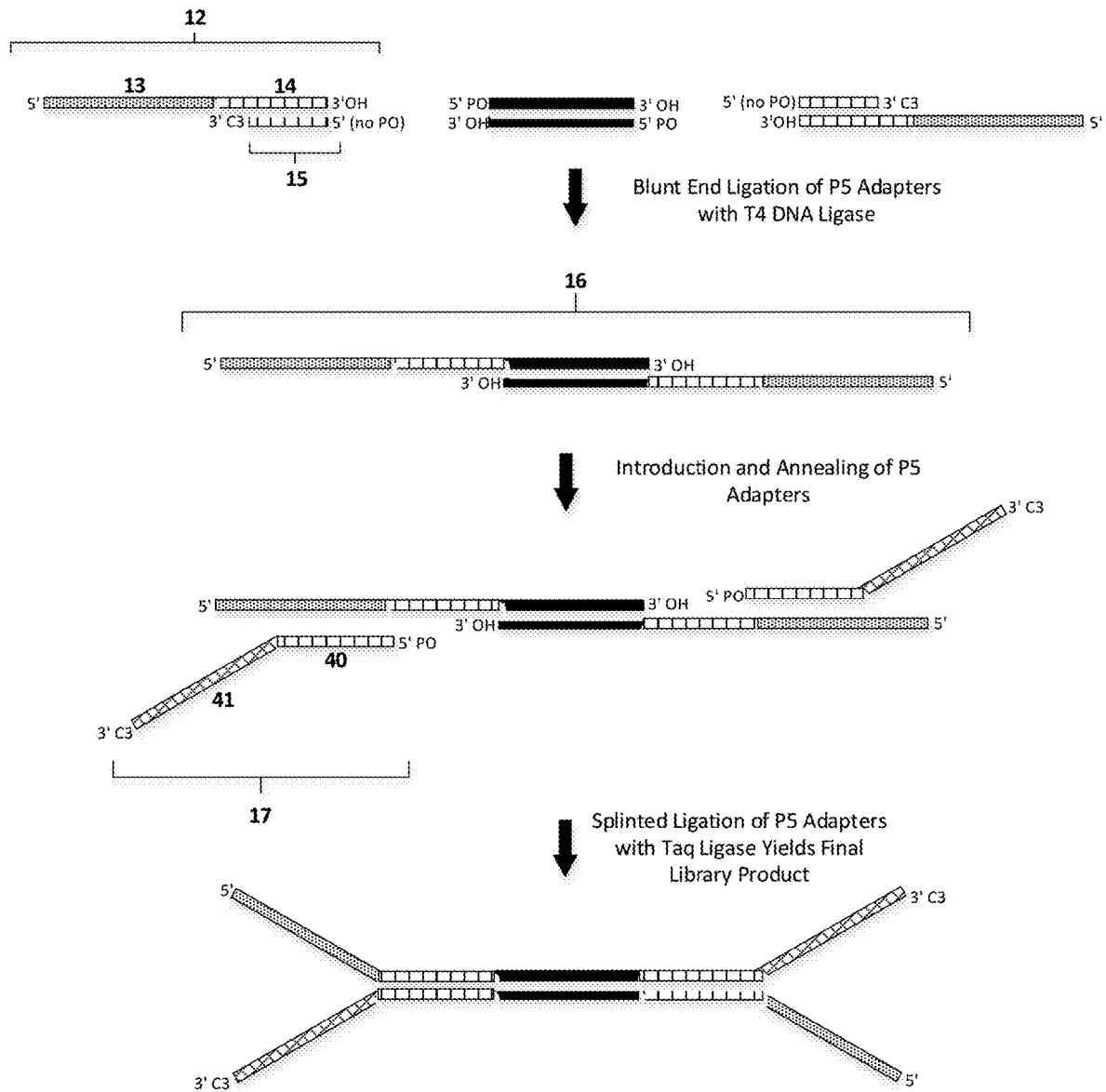
FIG. 4 is a schematic demonstrating an exemplary embodiment of the CSD method. The first step consists of the attachment of a first sequencing adapter (12) to the DNA target fragment via blunt end ligation catalyzed by T4 DNA ligase. Said first sequencing adapter consists of a first and second DNA strand. The first DNA strand has a 3' OH group on its 3' end and consists of a first sequence (14) which is complementary to, but longer than, the second DNA strand (15) and a second, non-complementary tag sequence (13) that contains the first sequencing primer binding site and, optionally, a UMI and/or sample barcode sequence. The second DNA strand (15) is a truncated oligonucleotide with a C3 blocking group at its 3' end, a dephosphorylated 5' end, and serves to facilitate the blunt end ligation of the 5' PO of the target fragment with the 3' OH of the first strand of the first sequencing adapter, leading to the first ligation product (16). The second step consists of the attachment of a second sequencing adapter (17) to the first ligation product via splint end ligation catalyzed by Taq ligase. Said second sequencing adapter has a 5' PO and consists of a first sequence (40) that is complementary to the first sequence (14) of the first sequencing adapter and a second sequence (41) that contains the second sequencing primer binding site and, optionally, a second UMI and/or sample barcode sequence. Since the length of the complementary sequence of the second adapter (40) is longer than that of the truncated oligo of the first adapter (15), the second adapter is able to displace the truncated oligo during the annealing step that precedes the splint end ligation. The splint end ligation leads to the final library product.

In a fourth embodiment of the CSD method, sequencing adapters can be ligated to the 5' end of inserts first (FIG. 4). In this embodiment, the 3' end of the first sequencing adapter (P5 or P7 for Illumina sequencing) is attached to the 5' end of phosphorylated inserts via blunt ligation. To prevent dimer formation, this adapter is not 5' phosphorylated in the double-stranded portion, so it will not ligate to inserts or other adapter molecules. The second adapter sequence (P5 or P7 for Illumina sequencing) is attached to the 3' end of inserts via splinted ligation using a single-stranded oligo that has phosphate groups on the 5' ends and C3 spacers on the 3' ends. This ligation can be performed using Taq DNA ligase, or any other ligase capable of performing splinted ligations with little activity on blunt-ended substrates (Amp-ligase, 9° N, Tth, etc.). Since the ligase prefers splinted ligation, adapter dimers are minimized, which mitigates the need for size-selection post-ligation.

Figure 5:
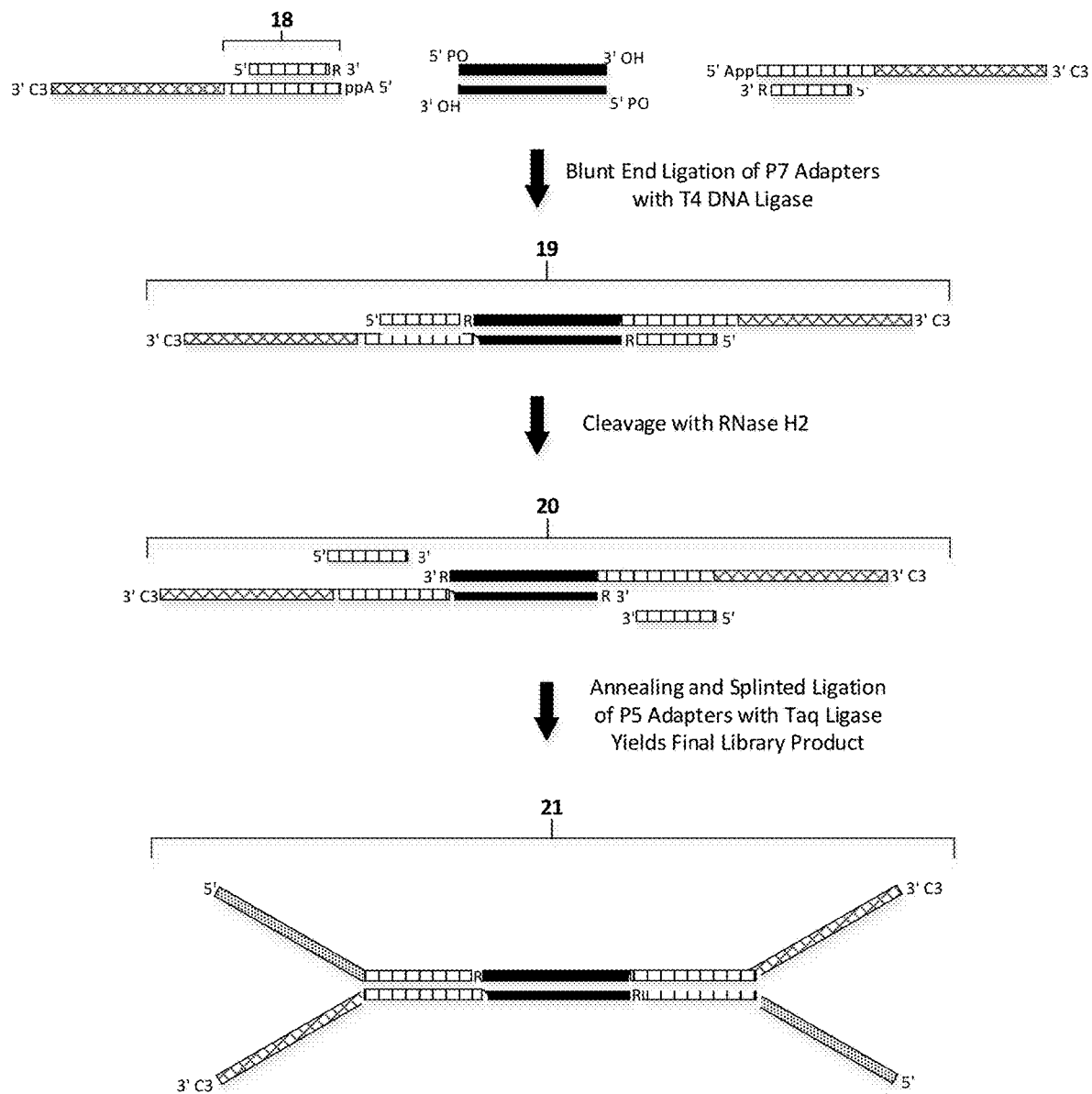
FIG. 5 is a schematic demonstrating an exemplary embodiment of the CSD method. The elements of the fifth embodiment are similar to those of the second embodiment, the difference being that the truncated second strand (18) of the first sequencing adapter has an RNA residue at its 3' end. Said first sequencing adapter is then attached to the DNA target fragment via blunt end ligation catalyzed by the K159S mutant T4 DNA ligase. Unlike the previous embodiments, both the first and second strands of the first sequencing adapter are ligated to the target fragment, the truncated second strand being ligated, via its 3'R, to the 5' PO of the target fragment, resulting in a first ligation product (19). The truncated second strands are then removed via RNase H2 cleavage, which occurs at the phosphodiester bond on the 5' side of an RNA residue. The resulting product (20) is similar to the first ligation product of the previous embodiments, the difference being that it has 3' RNA residues. Said 3' RNA residues are then ligated to the 5' PO ends of the second sequencing adapters during the second ligation step, resulting in a library product (21) with internal RNA residues.

In a fifth embodiment of the CSD method, there is an RNA base on the 3' end of the truncated ligation helper oligonucleotide, instead of a ddN. In this case, both the 5' end of the adapter and the 3' end of the truncated stem are ligated to the insert. However, the stem is then cleaved off via the activity of an RNase H2 enzyme which cleaves 5' of the RNA base. After an SPRI cleanup step, the second ligation takes place (FIG. 5).

Figure 6:
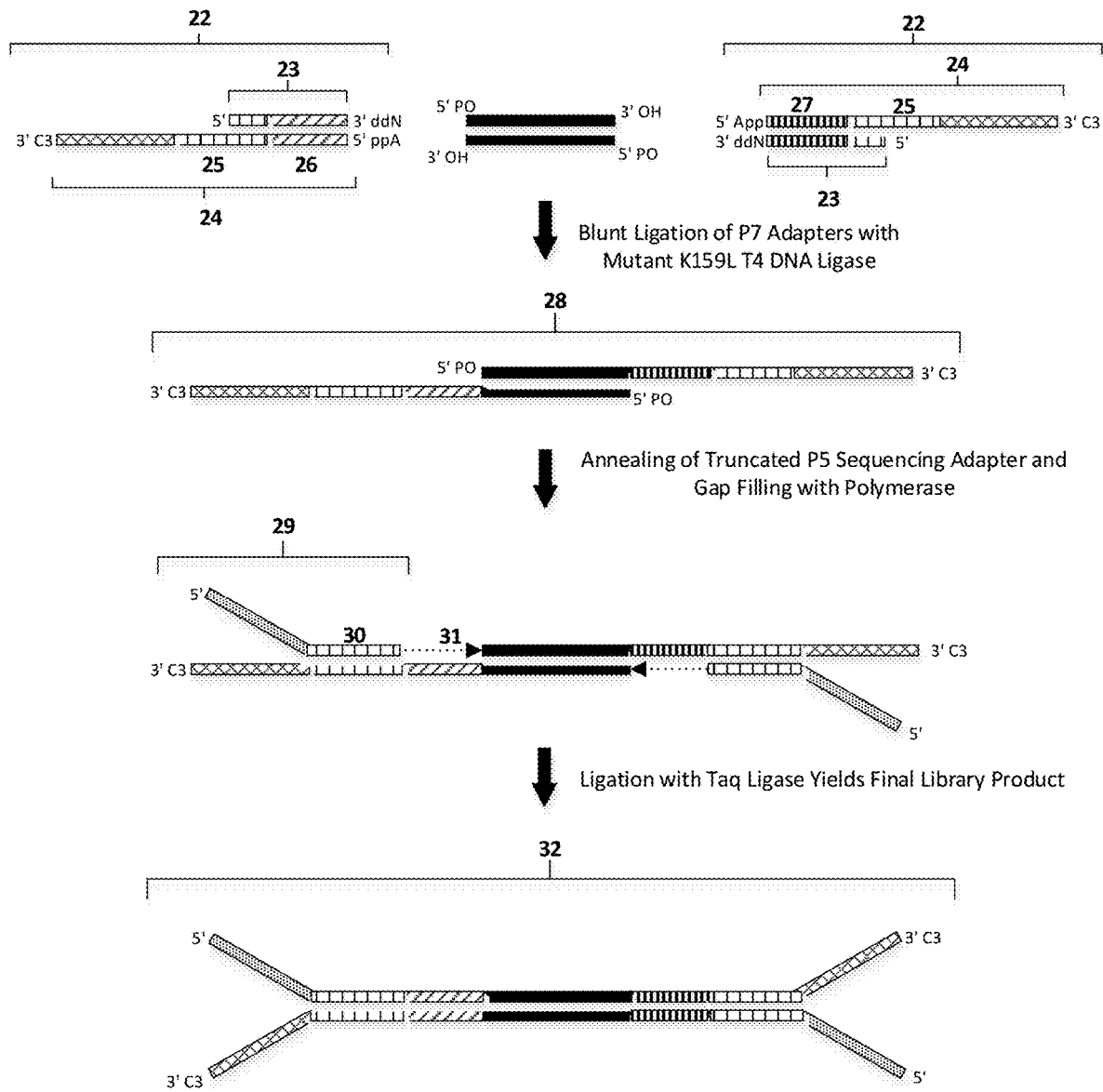
FIG. 6 is a schematic demonstrating an exemplary embodiment of the CSD method. The elements of the sixth embodiment are similar to those of the second embodiment, albeit with the following differences. In this embodiment, the first DNA strand (24) of the first sequencing adapter (22) contains a variable tag sequence (26, 27) on its 5' end. This serves to differentially label the sense and antisense strands of the target fragments during the first ligation step, leading to a first ligation product with each strand labeled differently (28). As with the previous embodiments, blunt end ligation is enhanced using a blocked and truncated second strand (23) that, in this embodiment, is complementary to the variable region (26, 27) and part of the constant region (25) of the first DNA strand (24). During the second ligation step, the second sequencing adapter (29) anneals to the first ligation product via its sequence (30) that is complementary to the constant sequence added by the first sequencing adapter (31), but not to the variable region (26, 27). This results in a gap that is filled in with a DNA polymerase and a DNA ligase (31), leading to a final library product (32) with its sense and antisense strands labelled differently.
Figure 7:
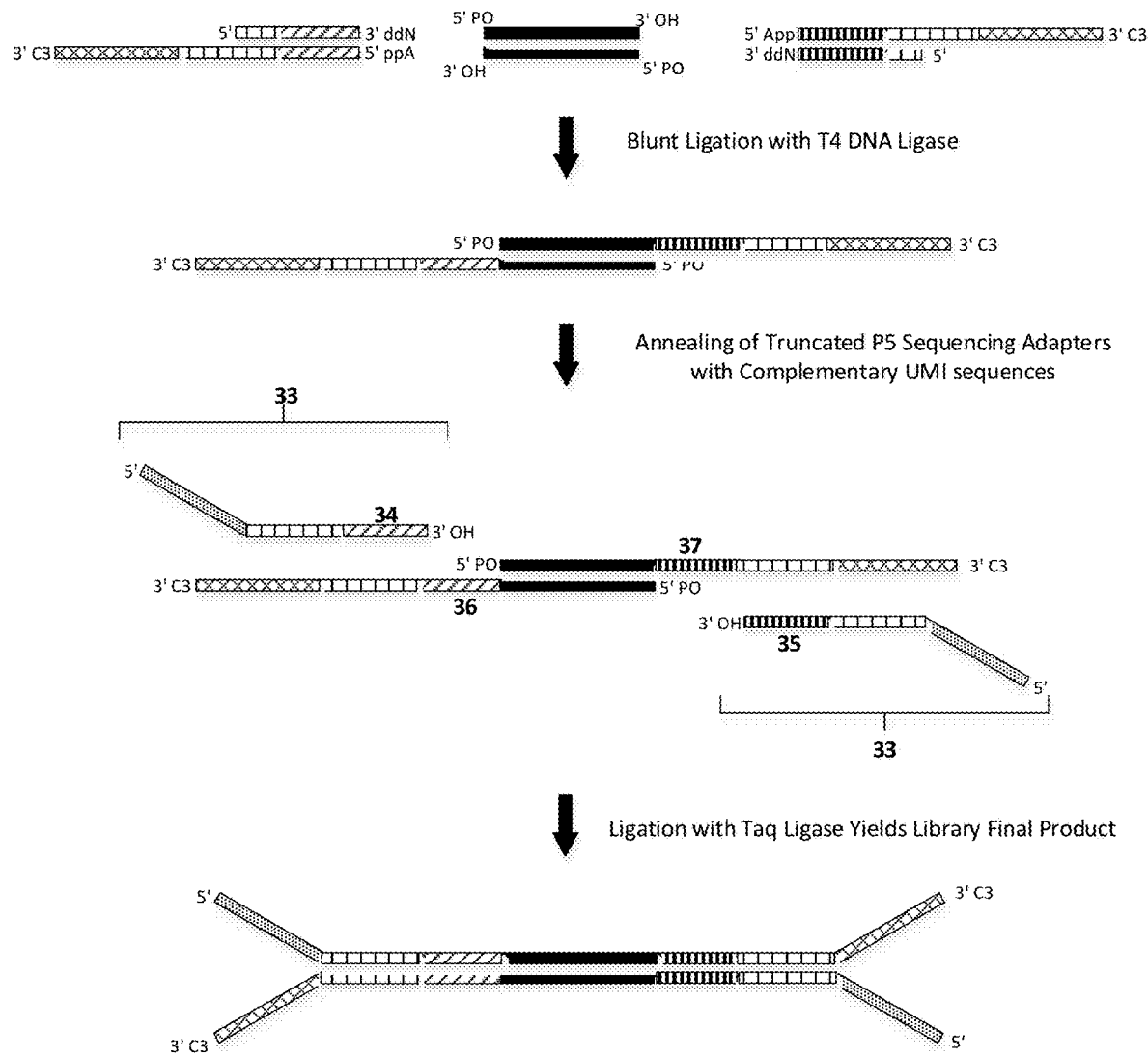
FIG. 7 is a schematic demonstrating an exemplary embodiment of the CSD method. The elements of the seventh embodiment are similar to those of the sixth embodiment, the difference being that the second sequencing adapter (33) has an additional sequence (34, 35) that is complementary to the variable tag sequence (36, 37) added by the first sequencing adapter. As a result, no gap is created after the second sequencing adapter anneals to the first ligation product and no polymerase step is needed.

In a sixth embodiment of the CSD method, the first sequencing adapter has a tag sequence on its 5' end which serves to independently label the sense and antisense strands of the target on their 3' ends (FIG. 6 and FIG. 7). These sequence tags are not limited to any particular length or sequence. The bases can be degenerate, fixed, or a combination of both. Modified bases can also be used. As before, the 5' end of the adapter is pre-adenylated and ligated on to the repaired 3' end of the target by either the K159S mutant T4 DNA ligase, or via a wildtype T4 ligase in the absence of ATP. The second sequencing adapter is then annealed to the ligated first adapter at its complementary stem sequence, leaving a gap which spans the tag sequence. The gap is then filled in with a polymerase, creating an in situ UMI which is complementary to the first UMI. After the fill in step, the 3' end of the newly created in situ UMI is ligated on to the 5' end of the target fragment. Optionally, this is followed by a PCR amplification step using primers that prime off of the first and second adapter sequences and may optionally add additional sequences such as sample barcodes and/or P5/P7 sequences. Representative examples of the first strand of the first sequencing adapter for the sixth embodiment are provided as SEQ ID NOs:18-33. Representative examples of the second strand of the first sequencing adapter for the sixth embodiment are provided as SEQ ID NOs:34-49. A representative example of the second sequencing adapter for the sixth embodiment is provided as SEQ ID NO:50. Representative examples of optional forward and reverse primers that could be used for the PCR amplification step of the sixth embodiment are provided as SEQ ID NOs:75-98, and SEQ ID NOs:51-74, respectively. These particular representative forward and reverse PCR primers contain P5 and P7 adapter sequences, respectively, as well as sample barcode sequences. All representative examples for the sixth embodiment are offered to illustrate, but not to limit, the claimed method.

The seventh embodiment of the CSD method is a variation of the sixth embodiment in which the second sequencing adapter has an additional sequence that is complementary to tag sequence added during the first ligation step (FIG. 7). As a result, no gap is present after the second sequencing adapter anneals to the first ligation product and the fill-in step with a DNA polymerase is unnecessary prior to ligation. This can be accomplished by using a finite number of variable tags. For example, this embodiment could potentially consist of a plurality of first sequencing adapters, each with one of 24 distinct variable tag sequences, and a plurality of second sequencing adapters, each with one of 24 distinct sequences which are complementary to the variable sequences of the first sequencing adapters.

In any of the above embodiments, unique molecular identifiers (UMIs) and sample barcodes can be incorporated into one or both of the sequencing adapters. Molecular identifiers can be constructed using fixed or degenerate sequences of any length compatible with Illumina sequencers.

In any of the above embodiments, one or more of the sequencing adapters used for the first and/or second ligations are shortened versions of the full sequencing adapters, in which case the remaining parts of the sequencing adapters are added later via PCR with tailed primers.

The CSD methods described herein can be used for any application involving DNA sequencing, but is especially valuable for cancer diagnostics where detection of rare variants in mixed populations of tumor and normal DNA is crucial. The CSD methods can also be used to construct sequencing libraries from Formalin-Fixed Paraffin-Embedded (FFPE) samples. The invention can also be used to construct sequencing libraries from ultra-low inputs of DNA with or without PCR, which may aid in forensic or microbiological studies where limited quantities of DNA are available and/or PCR cannot be tolerated.

Unlike the prior art which requires size-selection due to formation of adapter dimers, the CSD methods described herein feature a ligation strategy that does not require size selection. Lack of size-selection enables superior recovery of DNA, which greatly increases library complexity/coverage and sensitivity to low frequency variants. Adapter dimers are also problematic for library quantification and sequencing, because standard methods of DNA quantification are greatly skewed by their presence. This can cause suboptimal cluster density and significantly reduce the number of reads aligning to actual samples, which increases sequencing costs. Also, unlike the prior art, the embodiment of the invention employing K159S does not create chimeras via ligation, which should greatly improve detection of rare structural variants associated with cancer.

Although initial work has focused on attachment of P5 and P7 adapters for Illumina sequencing, the CSD methods described herein could be used on alternate platforms which also require the attachment of one or more synthetic sequences (Ion Torrent® sequencing platform for example).

IV. Examples

Example 1

Figure 8A:
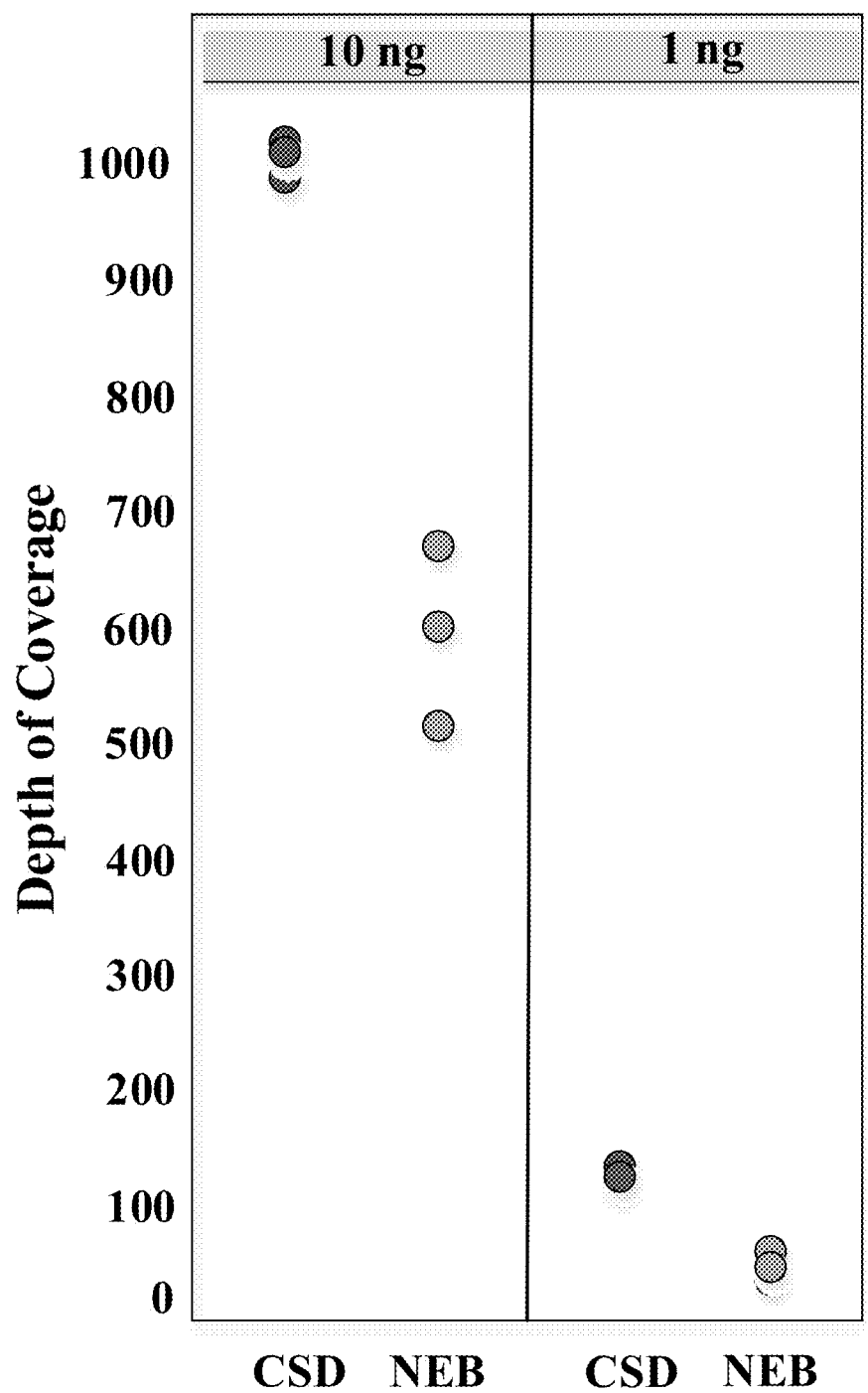
FIG. 8A is a graph showing depth of coverage values for each of three replicate libraries, obtained using the method described in Example 1, plotted for CSD (dark gray circles) and NEB (light gray circles) for 10 ng (left side) and 1 ng (right side) of DNA input. For the 10 ng DNA input, the average depth of coverage for CSD was 1009×, vs 598× for NEB. For the 1 ng DNA input, the average depth of coverage for CSD was 131×, vs 53× for NEB.
Figure 8B:
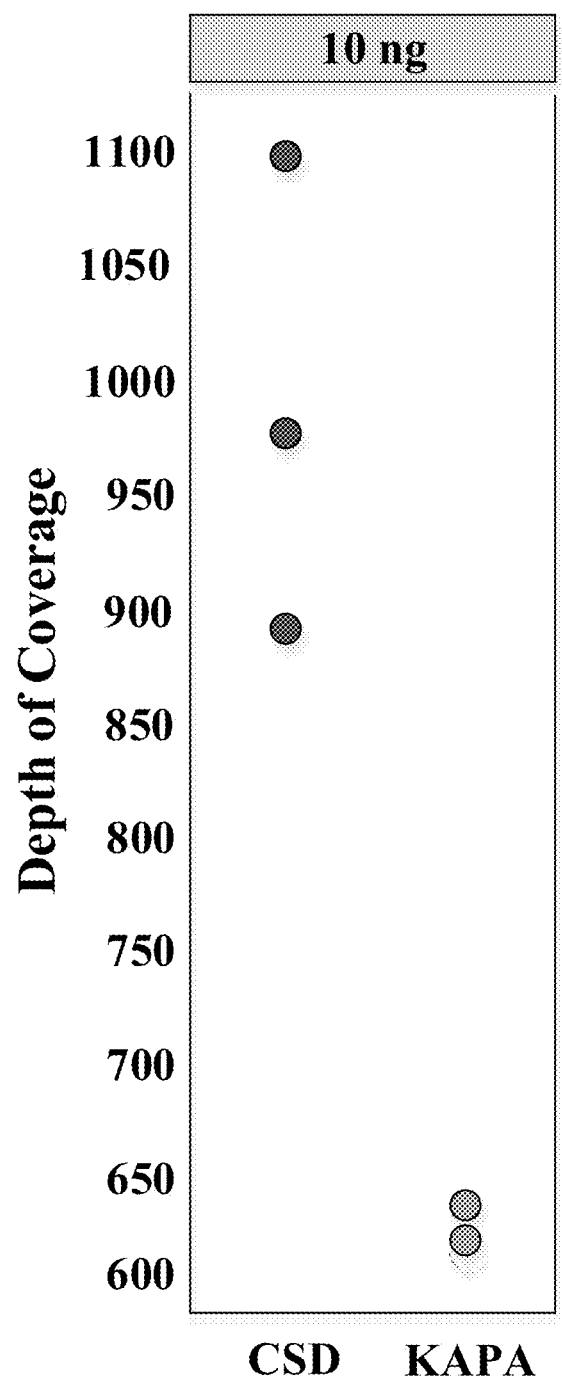
FIG. 8B is a graph showing depth of coverage values for each of three replicate libraries, obtained from the experiment described in Example 1, plotted for CSD (dark gray circles) and Kapa (light gray circles). The average depth of coverage for CSD was 1006×, vs 628× for Kapa.

This example demonstrates the enhanced depth of coverage obtained from NGS libraries, prepared from high quality genomic DNA, using the second embodiment of the CSD method as compared to that obtained when using either the NEB® Ultra™ II library (New England BioLabs) or Kapa Hyper Prep (Kapa Biosystems) methods. The high quality genomic DNA was extracted from cell line NA12878 (ATCC). Either 1 or 10 ng of the extracted DNA was sheared to an average size of 150 bp using ultrasonic fragmentation (Covaris S220) and then subjected to end-repair, which included phosphorylation of the 5' ends with T4 Polynucleotide Kinase (PNK), for 30 minutes, followed by purification via 2.5× AMPure beads. For the CSD treatment, P7 adapters (SEQ ID NOs:11-16), hybridized to truncated, 3' ddN blocked oligonucleotides (SEQ ID NO:17), were ligated onto the end repaired target fragments via blunt end ligation using the mutant K159S T4 DNA ligase for 15 minutes, followed by a 15 minute heat kill step. P5 adapters (SEQ ID NO:1 or SEQ ID NO:2) were then ligated onto the first ligation product using Taq DNA ligase for 15 minutes, followed by purification using 2.5× AMPure beads. For the NGS treatment, libraries were prepared as per manufacturer's instructions. Both libraries were then subjected to a PCR-amplification with primers that contain sequences that are complimentary to the P5 and P7 adapters under the following conditions: 98° C. for 45 seconds, 12 cycles of: 98° C. 15 s, 60° C. for 30 seconds, 72° C. for 30 seconds, 72° C. for 1 minute, 4° C. hold. The libraries then underwent hybrid capture, using a custom panel of around 800 IDT Lockdown probes, to pull down fragments containing target sequences that were used to determine the depth of coverage values. The resulting, target enriched product was purified via 1.8× AMPure beads and sequenced on a MiSeq® sequencer (Illumina) using 2×150 paired-end reads and following the manufacturer's protocol. The libraries were prepared in triplicate. Depth of coverage values for each of the three libraries obtained from CSD for 10 and 1 ng of DNA input, are plotted in comparison to those values obtained from the NEB (FIG. 8A) and Kapa (FIG. 8B) methods. When compared with the NEB method, the average depth of coverage for CSD was 1.7× higher with 10 ng of DNA input, and 2.5× higher with 1 ng of DNA input (FIG. 8A). When compared with the Kapa method, with 10 ng of DNA input, the average depth of coverage for CSD was 1.6× higher (FIG. 8B). Depth of coverage values were determined by the number of unique reads (not counting PCR duplicates) that mapped to the expected target sequences that were enriched for via the 800 probe lockdown panel.

Example 2

Figure 8C:
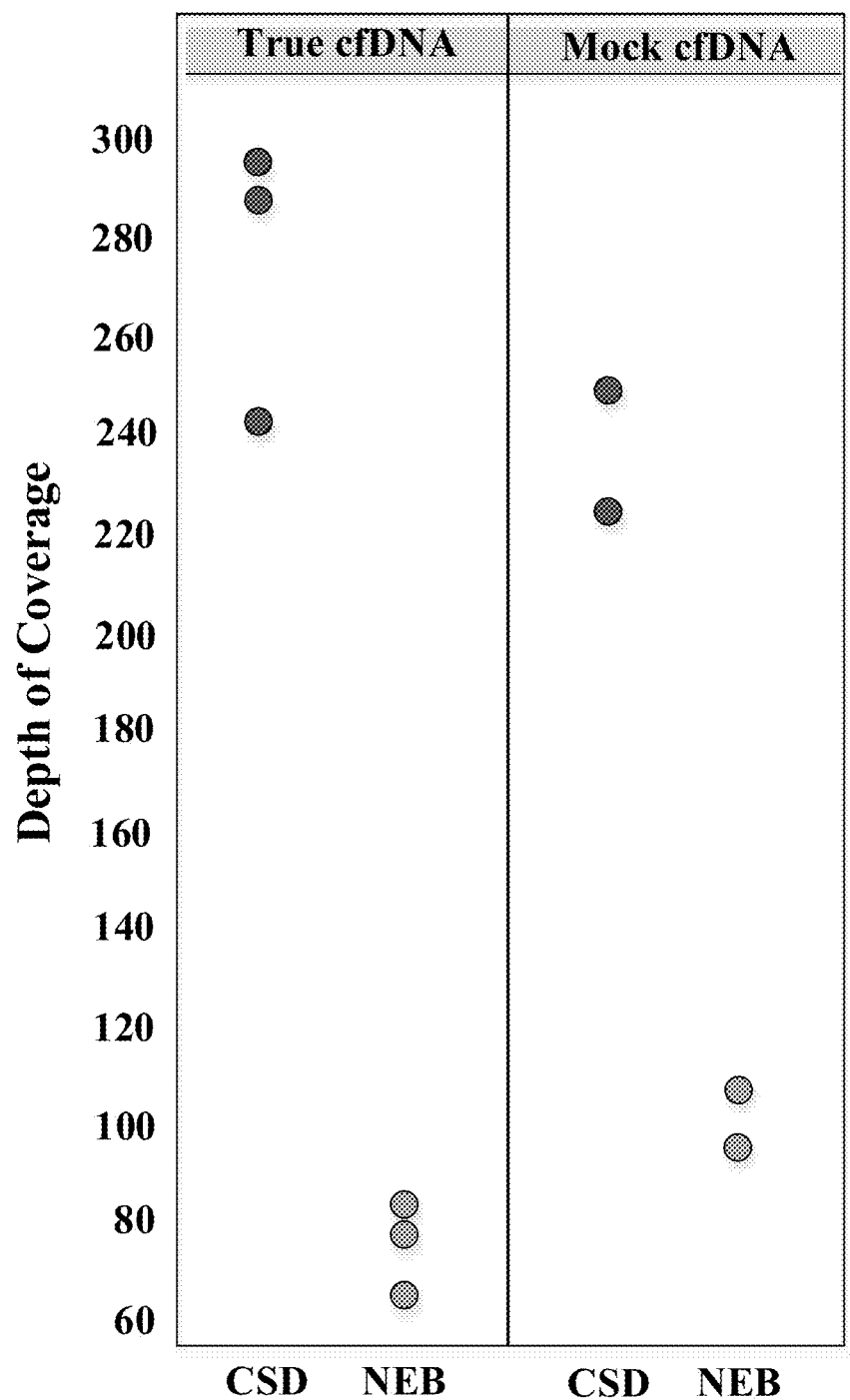
FIG. 8C is a graph showing depth of coverage values for each of three replicate libraries, obtained from the experiment described in Example 2, plotted for CSD (dark gray circles) and NEB (light gray circles) for libraries derived from the "true" (left side) and "mock" (right side) cfDNA. For the "true" DNA input, the average depth of coverage for CSD was 276×, vs 77× for NEB. For the "mock" DNA input, the average depth of coverage for CSD was 241×, vs 104× for NEB.

This example demonstrates the enhanced depth of coverage obtained from NGS libraries, prepared from circulating cell free DNA (cfDNA), using the second embodiment of the CSD method as compared to that obtained when using the NEBNext® Ultra™ II library. "True" cfDNA samples are real cell-free DNA isolated by Biochain from healthy individuals, while "mock" cfDNA samples are cell-line genomic DNA (NA12878) sheared to 150 bp using a Covaris S2. Libraries were prepared with 1 ng of the cfDNA using the CSD and NEB methods, as described in Example 1, in triplicate. When compared with the NEB method, the average depth of coverage for CSD was 3.6× higher with the "true" cfDNA input, and 2.3× higher with the "mock" cfDNA input (FIG. 8C).

Example 3

Figure 8D:
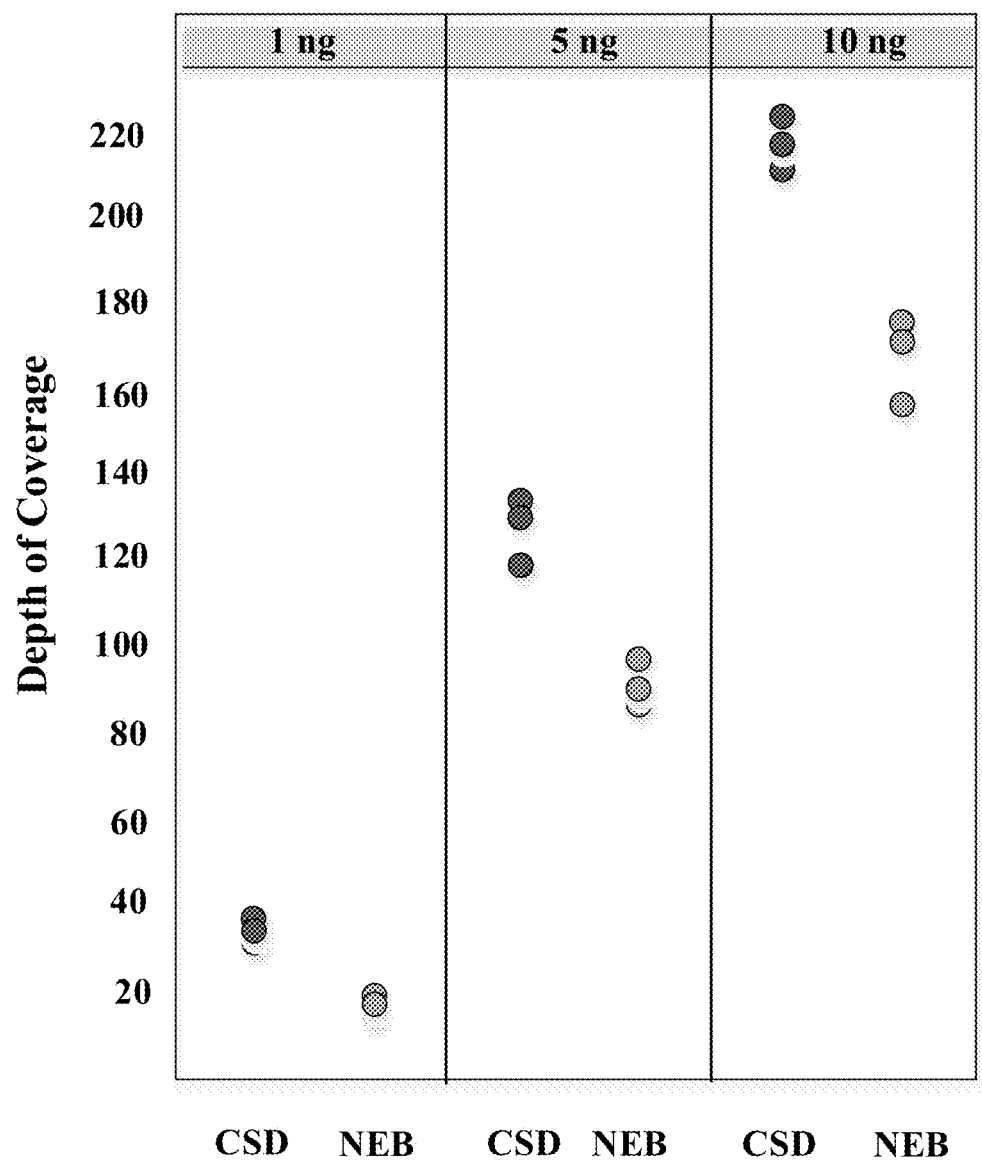
FIG. 8D is a graph showing depth of coverage values for each of three replicate libraries, obtained from the experiment described in Example 3, plotted for CSD (dark gray) and NEB (light gray) for 1 ng (left side), 5 ng (middle) and 10 ng (right side) of DNA input. When compared with the NEB method, the average depth of coverage for CSD was 1.8×, 1.4×, and 1.3× higher with the 1 ng, 5 ng, or 10 ng of the FFPE derived genomic DNA, respectively.

This example demonstrates the enhanced depth of coverage obtained from NGS libraries, prepared from low quality genomic DNA extracted from FFPE samples, using the second embodiment of the CSD method as compared to that obtained when using either the NEB Ultra II library. The FFPE samples were procured from Asterand Bioscience. Libraries were prepared as described above using 1 ng, 5 ng, or 10 ng of the FFPE derived genomic DNA, sheared to an average size of 200 bp, as starting material. When compared with the NEB method, the average depth of coverage for CSD was 1.8×, 1.4×, and 1.3× higher with the 1 ng, 5 ng, or 10 ng of the FFPE derived genomic DNA, respectively (FIG. 8D).

Example 4

This example demonstrates the enhanced depth of coverage obtained from NGS libraries, prepared from low quality genomic DNA extracted from FFPE samples, using the second embodiment of the CSD method as compared to that obtained when using either the NEB Ultra II library. The FFPE samples were procured from Asterand Bioscience. Libraries were prepared as described above using 1 ng, 5 ng, or 10 ng of the FFPE derived genomic DNA, sheared to an average size of 200 bp, as starting material. When compared with the NEB method, the average depth of coverage for CSD was 1.8×, 1.4×, and 1.3× higher with the 1 ng, 5 ng, or 10 ng of the FFPE derived genomic DNA, respectively (FIG. 8D).

Example 5

Figure 9:
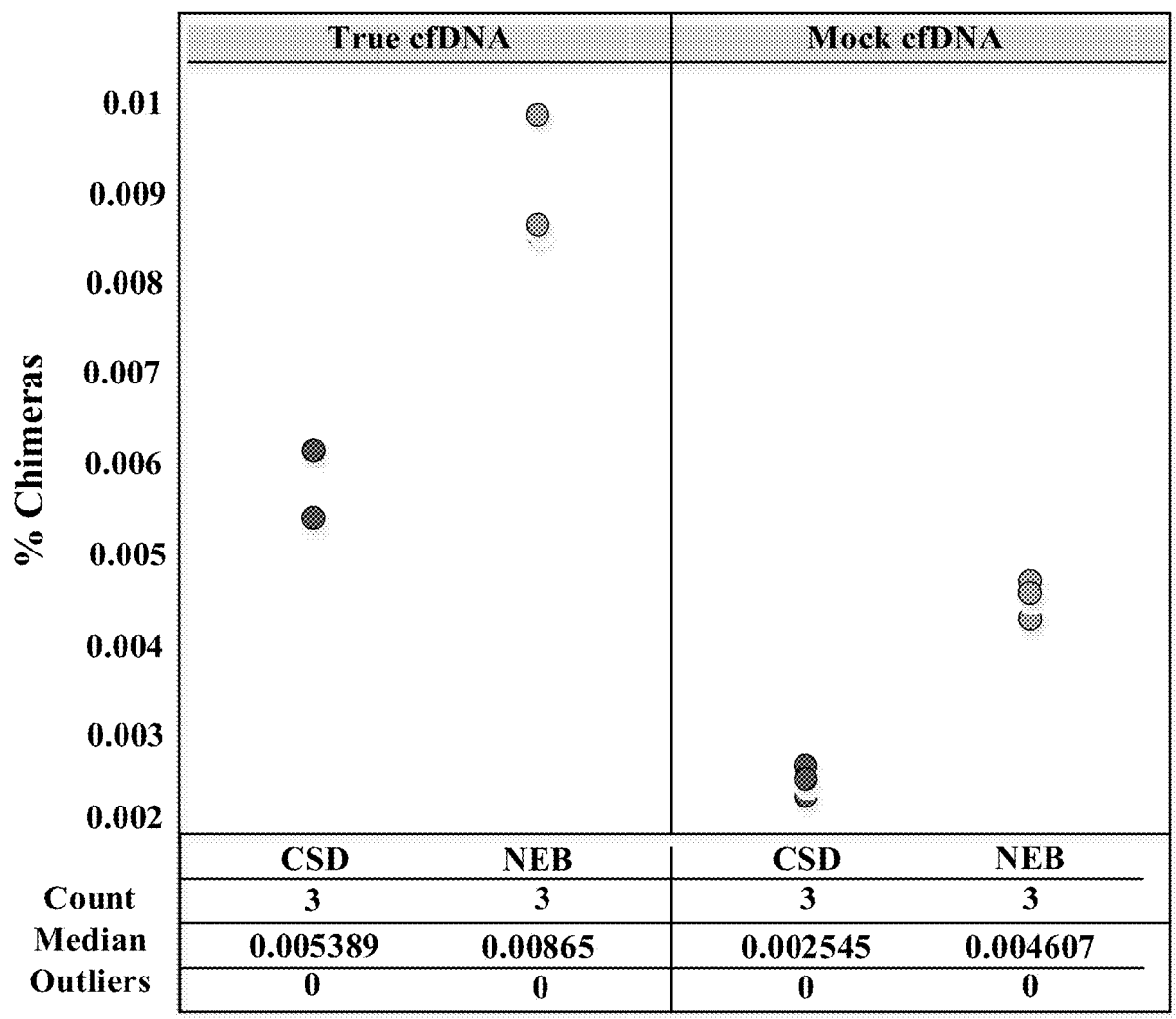
FIG. 9 is a graph showing percent chimera values for each of three replicate libraries obtained from the experiment described in Example 4, plotted for CSD (dark gray) and NEB (light gray) for libraries derived from the "true" (left side) and "mock" (right side) cfDNA. When compared with the NEB method, the average % of chimeras present for CSD was 1.6× lower with the "true" cfDNA input and 1.8× lower with the "mock" cfDNA input.

This example demonstrates the reduced chimera rate in NGS libraries prepared from cfDNA using the second embodiment of the CSD method as compared to that present in cfDNA libraries prepared using the NEB method. Libraries were prepared as described above, using 1 ng of "true" or "mock" cfDNA as input, in triplicate. When compared with the NEB method, the average % of chimeras present for CSD was 1.6× lower with the "true" cfDNA input and 1.8× lower with the "mock" cfDNA input (FIG. 9). The % chimera values were calculated based on the number of unique reads that were improperly aligned with the reference sequence (hg19). Fragments categorized as "chimeric" have either (1) paired reads that face the same direction (same orientation), (2) paired reads that align to regions of the reference sequence that are greater than 3 kb apart, and/or (3) paired reads that align to different chromosomes.

Example 6

Figure 10A:
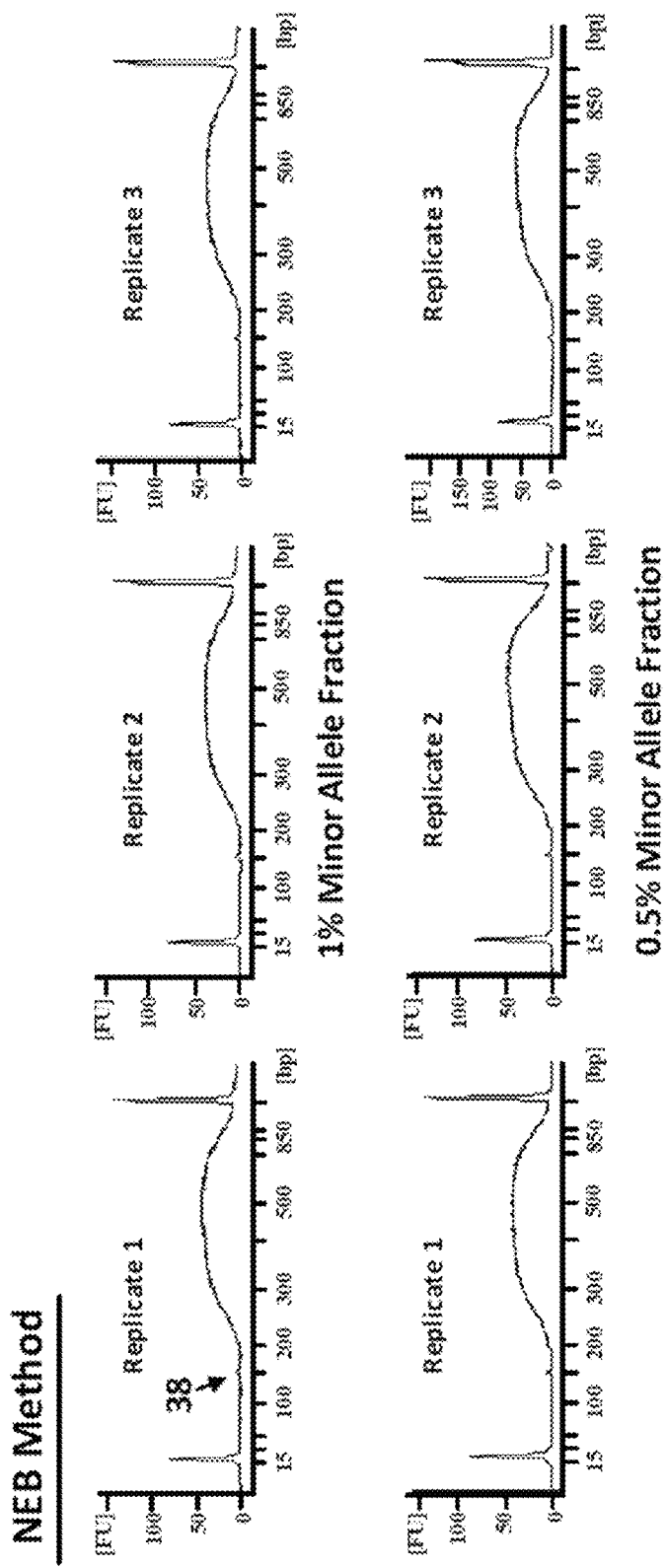
FIG. 10A and FIG. 10B show traces, generated with a Bioanalyzer DNA1000 chip, that show the size distribution of DNA molecules present in each of three replicate libraries generated with the NEB (FIG. 10A) or CSD (FIG. 10B) methods from the sample DNA with 1% or 0.5% minor allele fractions. The absence of dimer peaks at the 150 bp mark (39) for the CSD method, and presence of such peaks in the NEB method (38), demonstrates the reduced occurrence or adapter dimers for libraries prepared with CSD, when compared to those prepared with the NEB method.

This example demonstrates the reduced occurrence of adapter dimers in NGS libraries prepared from high quality genomic DNA when using the second embodiment of the CSD method as compared to that present in libraries prepared using the NEB method. The high quality genomic DNA samples were extracted from two cell-lines, NA12878 and NA24385, and mixed at two different ratios, resulting it two mixtures having 1% and 0.5% minor allele fractions, respectively. Samples were sheared to 300 bp fragments. NEB libraries were created using a 0.9× AMPure ratio post-ligation, which is meant to size select away adapter-dimer. CSD libraries were created with a 2.5× ratio post-ligation, which is too high to effectively remove full length adapter dimers. NEB libraries were treated with 1.0× AMPure post-PCR to remove any residual dimer, while CSD libraries were treated with a 1.8× ratio. The final library products were analyzed on a Bioanalyzer DNA1000 chip, by which traces were generated that showed the size distribution of DNA molecules present in each library. The absence of dimer peaks at the 150 bp mark for the CSD method without size selection indicates dimer formation is negligible or non-existent in libraries prepared with the CSD method (FIG. 10A). Libraries prepared using the NEB method, on the other hand, still contain small amounts of adapter dimer, despite two size selection steps, as is indicated by the small peaks at the 150 bp mark in the traces (FIG. 10A).

Example 7

Figure 10B:
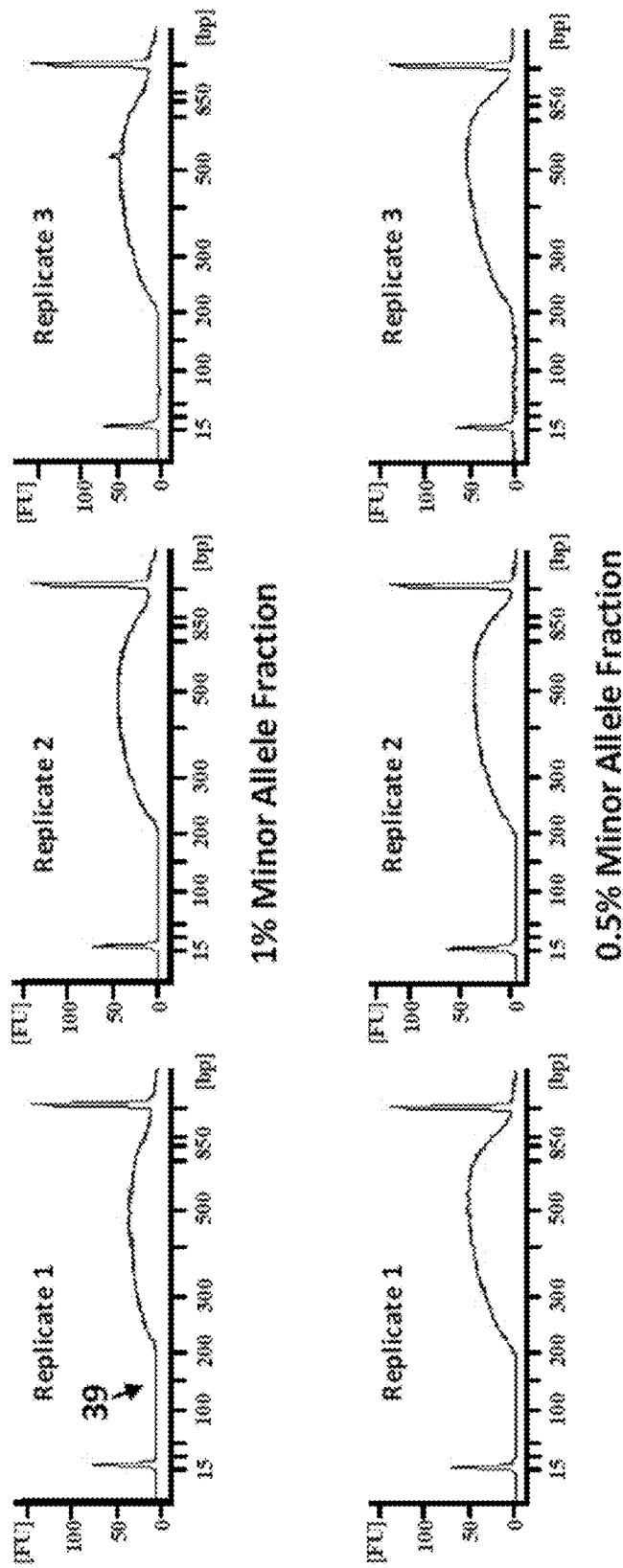

This example demonstrates that the reduced presence of adapter dimers in NGS libraries prepared using the second embodiment of the CSD method is independent of the lengths of the target fragments used as the starting point. Libraries were created as described above with 10 ng of high quality genomic DNA, extracted from cell line NA12878, and sheared to 150 bp, 200 bp, or 300 bp. As described above, the final library products were analyzed on a Bioanalyzer DNA1000 chip, generating size distribution traces. For all three fragment lengths, there was an absence of dimer peaks that are typically observed in the 125 bp-150 bp range (FIG. 10B).

Example 8

Figure 10C:
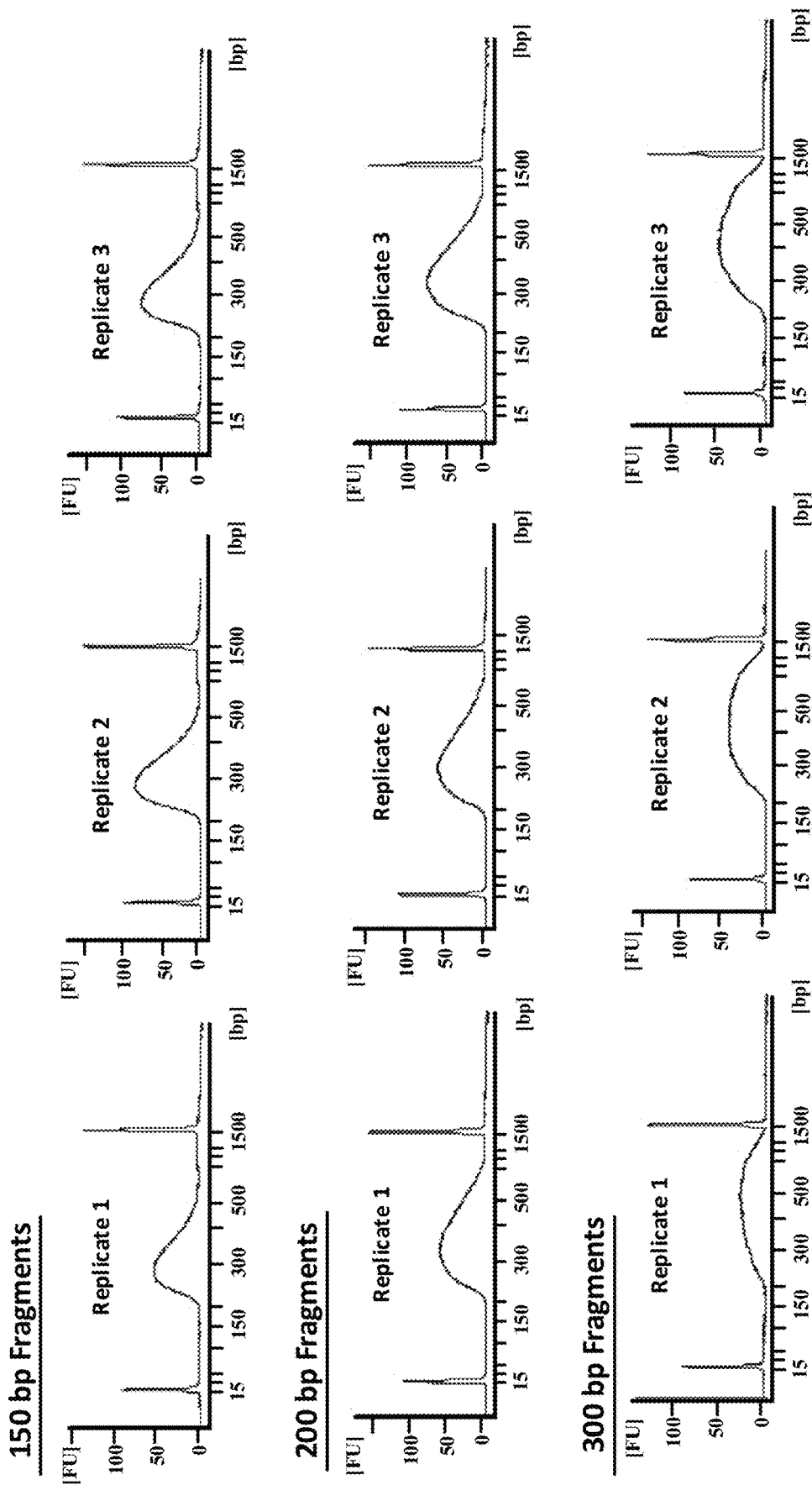
FIG. 10C shows traces generated with the Bioanalyzer DNA1000 chip (post-PCR) for each of three replicate libraries created with 10 ng of high quality genomic DNA sheared to 150 bp, 200 bp, or 300 bp (gDNA extracted from cell line NA12878 procured from ATCC). For all three fragment lengths, there was an absence of dimer peaks that are typically observed in the 125 bp-150 bp range.
Figure 10D:
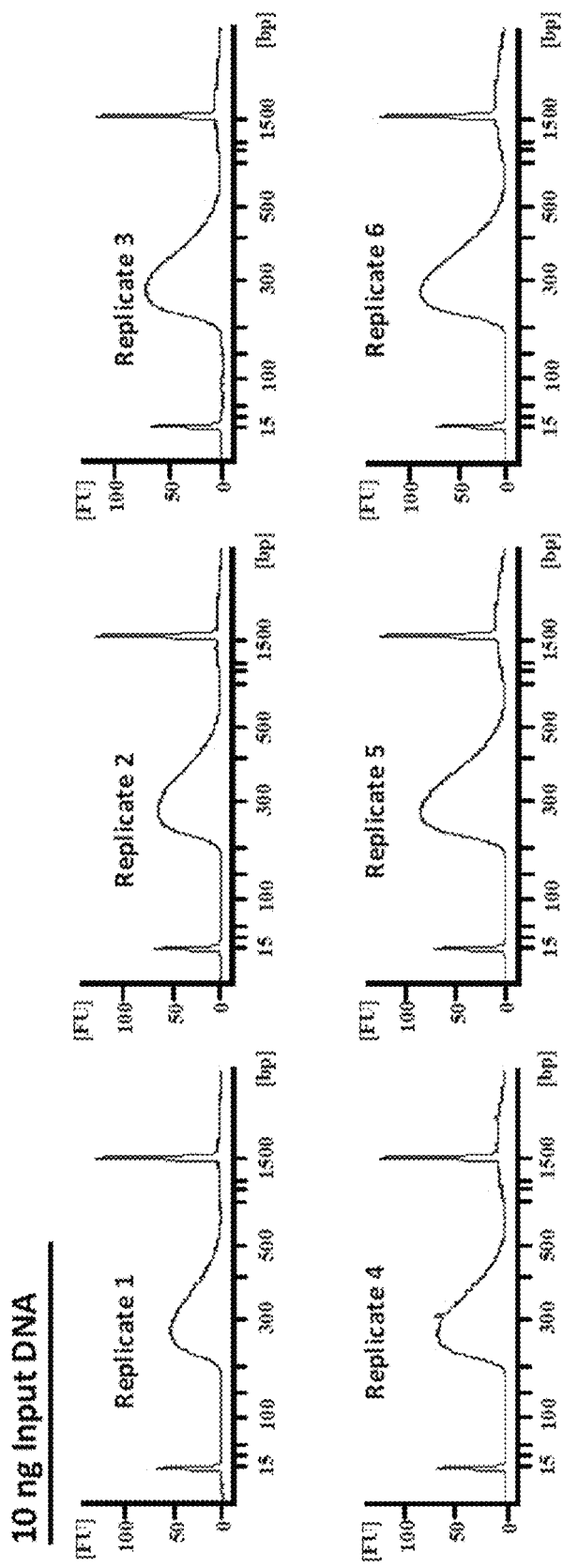
FIG. 10D and FIG. 10E shows traces generated with the Bioanalyzer DNA1000 chip (post-PCR) for each of three replicate libraries created with 10 ng (FIG. 10D) or 1 ng (FIG. 10E) of high quality genomic DNA sheared to 200 bp. For both input amounts, there was an absence of dimer peaks that are typically observed in the 125 bp-150 bp range.
Figure 10E:
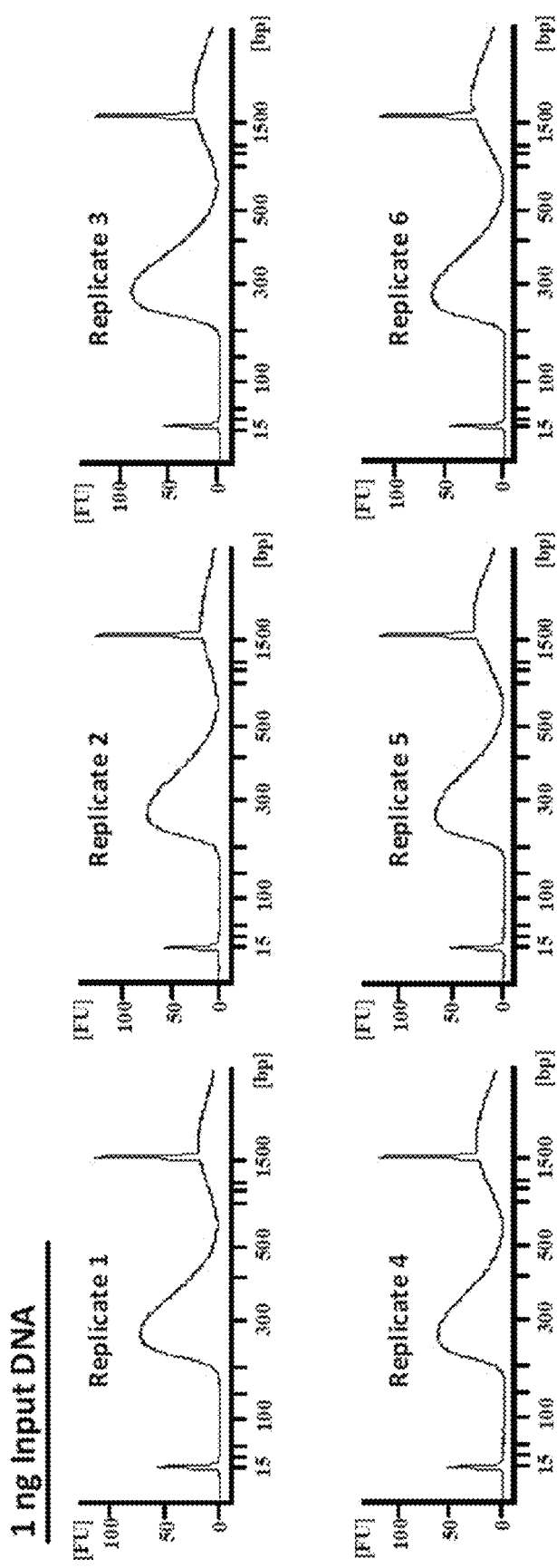

This example demonstrates that the reduced presence of adapter dimers in NGS libraries prepared using the second embodiment of the CSD method is independent of the amount of input DNA used as starting material. Libraries were created as described above with 10 ng or 1 ng of high quality genomic DNA, extracted from cell line NA12878, and sheared to 200 bp. For both input amounts, there was an absence of dimer peaks that are typically observed in the 125 bp-150 bp range (FIG. 10C). For reference, the secondary peak at about 1500 bp merged with the upper marker is a known phenomenon due to over-amplification during PCR.

Example 9

This example demonstrates the enhanced sensitivity achieved in NGS libraries prepared from high quality genomic DNA using the sixth embodiment of the CSD method as compared to that obtained when using the Kapa Hyper Prep method. The high quality genomic DNA was extracted from cell-lines NA12878 and NA24385 and mixed at a ratio of 1/100, generating a homozygous and heterozygous minor allele frequency of 1% and 0.5%, respectively. The genomic mixtures, with inputs ranging from 1 to 25 ng, were sheared to an average size of 150 bp using ultrasonic fragmentation (Covaris S220), and then subjected to end-repair, which included phosphorylation of the 5' ends with T4 Polynucleotide Kinase (PNK), for 30 minutes, followed by purification via 2.5× AMPure beads. For the CSD treatment, truncated P7 adapters (SEQ ID NOs:18-33), hybridized to truncated, 3' ddN blocked oligonucleotides (SEQ ID NOs:34-49), were ligated onto the end repaired target fragments via blunt end ligation using the mutant K159S T4 DNA ligase for 15 minutes, followed by a 15 minute heat kill step. Truncated P5 adapters (SEQ ID NO:50) were then annealed to the constant sequence added by the first sequencing adapter (25 in FIG. 6), but not to the variable region (26 and 27 in FIG. 6). The resulting gap was filled in using Taq DNA polymerase, followed by ligation with Taq DNA ligase. This was followed by purification using 2.5× AMPure beads. The product was then subjected to a PCR-amplification with tailed primers containing the remaining portions of the P7 and P5 adapter sequences. P7 tailed primer sequences are listed as SEQ ID NOs:51-74 while P5 tailed sequences are listed as SEQ ID Nos:75-98. PCR conditions were as follows: 98° C. for 45 seconds; 12 cycles of 98° C. for 15 s, 60° C. for 30 seconds, 72° C. for 30 seconds; 72° C. for 1 minute; 4° C. hold. For the Kapa treatment, libraries were prepared as per manufacturer's instructions. The libraries underwent hybrid capture, using a ~100 kb custom panel of IDT Lockdown® probes, to pull down subsets of the mixed genotypes. In these subsets, there were 291 known nucleotide differences between the NA12878 and NA24385 sequences and these were used to assess the sensitivities and PPVs of the two library prep methods. The libraries underwent ultra-deep sequencing on a MiSeq® sequencer (Illumina) using 2×150 paired-end reads and following the manufacturer's protocol. This was followed by variant calling, using VarDict software. While there were three false positives called with the Kapa library at 20 ng input, there were zero false positives called with the Kapa library at 10 ng DNA input and the CSD library at both 10 and 20 ng DNA input, resulting in a PPV of one for both libraries. The number of false negatives, however, was 3× lower when using the CSD libraries at 20 ng input and 2× lower at 10 ng input, when compared to those gotten using the Kapa libraries at the same amounts of input. The results are shown in Table 2.

TABLE 1

Sequences

P5 Adapter Sequences (used for 2$^{nd}$ ligation)

| | |
|---|---|
| SEQ ID NO: 1 | AATGATACGGCGACCACCGAGATCTACACTCTTTCCCTACACGACGCTCTTCCGATCT |
| SEQ ID NO: 2 | AATGATACGGCGACCACCGAGATCTACACNNNNNNNACACTCTTTCCCTACACGACGCTCTTCCGATCT |

TABLE 1-continued

| Sequences |
|---|
| P7 Adapter Sequences (used for 1st ligation) |

| SEQ ID NO: 3 | /5Phos/AGATCGGAAGAGCACACGTCTGAACTCCAGTCACNNNNNNATCACGATCTCGTATGCCGTCTTCTGCTTG |
|---|---|
| SEQ ID NO: 4 | /5Phos/AGATCGGAAGAGCACACGTCTGAACTCCAGTCACNNNNNNCGATGTATCTCGTATGCCGTCTTCTGCTTG |
| SEQ ID NO: 5 | /5Phos/AGATCGGAAGAGCACACGTCTGAACTCCAGTCACNNNNNNTTAGGCATCTCGTATGCCGTCTTCTGCTTG |
| SEQ ID NO: 6 | /5Phos/AGATCGGAAGAGCACACGTCTGAACTCCAGTCACNNNNNNTGACCAATCTCGTATGCCGTCTTCTGCTTG |
| SEQ ID NO: 7 | /5Phos/AGATCGGAAGAGCACACGTCTGAACTCCAGTCACNNNNNNACAGTGATCTCGTATGCCGTCTTCTGCTTG |
| SEQ ID NO: 8 | /5Phos/AGATCGGAAGAGCACACGTCTGAACTCCAGTCACNNNNNNGCCAATATCTCGTATGCCGTCTTCTGCTTG |
| SEQ ID NO: 9 | /5Phos/AGATCGGAAGAGCACACGTCTGAACTCCAGTCACNNNNNNCAGATCATCTCGTATGCCGTCTTCTGCTTG |
| SEQ ID NO: 10 | /5Phos/AGATCGGAAGAGCACACGTCTGAACTCCAGTCACNNNNNNACTTGAATCTCGTATGCCGTCTTCTGCTTG |
| SEQ ID NO: 11 | /5rApp/AGATCGGAAGAGCACACGTCTGAACTCCAGTCACaacggcggNNNNNNATCTCGTATGCCGTCTTCTGCTTG/3SpC3/ |
| SEQ ID NO: 12 | /5rApp/AGATCGGAAGAGCACACGTCTGAACTCCAGTCACcatccgttNNNNNNATCTCGTATGCCGTCTTCTGCTTG/3SpC3/ |
| SEQ ID NO: 13 | /5rApp/AGATCGGAAGAGCACACGTCTGAACTCCAGTCACcgaattggNNNNNNATCTCGTATGCCGTCTTCTGCTTG/3SpC3/ |
| SEQ ID NO: 14 | /5rApp/AGATCGGAAGAGCACACGTCTGAACTCCAGTCACttagaaccNNNNNNATCTCGTATGCCGTCTTCTGCTTG/3SpC3/ |
| SEQ ID NO: 15 | /5rApp/AGATCGGAAGAGCACACGTCTGAACTCCAGTCACggccaacgNNNNNNATCTCGTATGCCGTCTTCTGCTTG/3SpC3/ |
| SEQ ID NO: 16 | /5rApp/AGATCGGAAGAGCACACGTCTGAACTCCAGTCACtcttggttNNNNNNATCTCGTATGCCGTCTTCTGCTTG/3SpC3/ |

| Truncated strand of first adapter with blocked 3' |
|---|

| SEQ ID NO: 17 | CTCTTCCGATC/3ddT/ |
|---|---|

| Duplex CSD Ligation I Truncated P7 adapters |
|---|

| SEQ ID NO: 18 | /5rApp/ACGATCAGAGATCGGAAGAGCACACGTCTGAACTCCAGTCAC/3SpC3/ |
|---|---|
| SEQ ID NO: 19 | /5rApp/TCGAGAGTAGATCGGAAGAGCACACGTCTGAACTCCAGTCAC/3SpC3/ |
| SEQ ID NO: 20 | /5rApp/CTAGCTCAAGATCGGAAGAGCACACGTCTGAACTCCAGTCAC/3SpC3/ |
| SEQ ID NO: 21 | /5rApp/ATCGTCTCAGATCGGAAGAGCACACGTCTGAACTCCAGTCAC/3SpC3/ |
| SEQ ID NO: 22 | /5rApp/TCGACAAGAGATCGGAAGAGCACACGTCTGAACTCCAGTCAC/3SpC3/ |
| SEQ ID NO: 23 | /5rApp/CCTTGGAAAGATCGGAAGAGCACACGTCTGAACTCCAGTCAC/3SpC3/ |
| SEQ ID NO: 24 | /5rApp/ATCATGCGAGATCGGAAGAGCACACGTCTGAACTCCAGTCAC/3SpC3/ |
| SEQ ID NO: 25 | /5rApp/TGTTCCGTAGATCGGAAGAGCACACGTCTGAACTCCAGTCAC/3SpC3/ |

TABLE 1-continued

Sequences

| SEQ ID NO: 26 | /5rApp/ATTAGCCGAGATCGGAAGAGCACACGTCTGAACTCCAGTCAC/3SpC3/ |
| --- | --- |
| SEQ ID NO: 27 | /5rApp/CGATCGATAGATCGGAAGAGCACACGTCTGAACTCCAGTCAC/3SpC3/ |
| SEQ ID NO: 28 | /5rApp/GATCTTGCAGATCGGAAGAGCACACGTCTGAACTCCAGTCAC/3SpC3/ |
| SEQ ID NO: 29 | /5rApp/AGGATAGCAGATCGGAAGAGCACACGTCTGAACTCCAGTCAC/3SpC3/ |
| SEQ ID NO: 30 | /5rApp/GTAGCGTAAGATCGGAAGAGCACACGTCTGAACTCCAGTCAC/3SpC3/ |
| SEQ ID NO: 31 | /5rApp/AGAGTCCAAGATCGGAAGAGCACACGTCTGAACTCCAGTCAC/3SpC3/ |
| SEQ ID NO: 32 | /5rApp/GCTACTCTAGATCGGAAGAGCACACGTCTGAACTCCAGTCAC/3SpC3/ |
| SEQ ID NO: 33 | /5rApp/CTCTGGATAGATCGGAAGAGCACACGTCTGAACTCCAGTCAC/3SpC3/ |

Duplex CSD Ligation 1 dideoxy blocked strands

| SEQ ID NO: 34 | CTCTGATCG/3ddT/ |
| --- | --- |
| SEQ ID NO: 35 | CTACTCTCG/3ddA/ |
| SEQ ID NO: 36 | CTTGAGCTA/3ddG/ |
| SEQ ID NO: 37 | CTGAGACGA/3ddT/ |
| SEQ ID NO: 38 | CTCTTGTCG/3ddA/ |
| SEQ ID NO: 39 | CTTTCCAAG/3ddG/ |
| SEQ ID NO: 40 | CTCGCATGA/3ddT/ |
| SEQ ID NO: 41 | CTACGGAAC/3ddA/ |
| SEQ ID NO: 42 | CTCGGCTAA/3ddT/ |
| SEQ ID NO: 43 | CTATCGATC/3ddG/ |
| SEQ ID NO: 44 | CTGCAAGAT/3ddC/ |
| SEQ ID NO: 45 | CTGCTATCC/3ddT/ |
| SEQ ID NO: 46 | CTTACGCTA/3ddC/ |
| SEQ ID NO: 47 | CTTGGACTC/3ddT/ |
| SEQ ID NO: 48 | CTAGAGTAG/3ddC/ |
| SEQ ID NO: 49 | CTATCCAGA/3ddG/ |

Duplex CSD Ligation 2 Universal Primer Gap fill

| SEQ ID NO: 50 | ACACTCTTTCCCTACACGACGCTCTTCCGATCT |
| --- | --- |

Duplex CSD P7 Barcoded PCR Primers

| SEQ ID NO: 51 | CAAGCAGAAGACGGCATACGAGATctgatcgtGTGACTGGAGTTCAGACGTGT |
| --- | --- |
| SEQ ID NO: 52 | CAAGCAGAAGACGGCATACGAGATactctcgaGTGACTGGAGTTCAGACGTGT |
| SEQ ID NO: 53 | CAAGCAGAAGACGGCATACGAGATtgagctagGTGACTGGAGTTCAGACGTGT |
| SEQ ID NO: 54 | CAAGCAGAAGACGGCATACGAGATgagacgatGTGACTGGAGTTCAGACGTGT |
| SEQ ID NO: 55 | CAAGCAGAAGACGGCATACGAGATcttgtcgaGTGACTGGAGTTCAGACGTGT |
| SEQ ID NO: 56 | CAAGCAGAAGACGGCATACGAGATttccaaggGTGACTGGAGTTCAGACGTGT |
| SEQ ID NO: 57 | CAAGCAGAAGACGGCATACGAGATcgcatgatGTGACTGGAGTTCAGACGTGT |

TABLE 1-continued

Sequences

| | |
|---|---|
| SEQ ID NO: 58 | CAAGCAGAAGACGGCATACGAGATacggaacaGTGACTGGAGTTCAGACGTGT |
| SEQ ID NO: 59 | CAAGCAGAAGACGGCATACGAGATcggctaatGTGACTGGAGTTCAGACGTGT |
| SEQ ID NO: 60 | CAAGCAGAAGACGGCATACGAGATatcgatcgGTGACTGGAGTTCAGACGTGT |
| SEQ ID NO: 61 | CAAGCAGAAGACGGCATACGAGATgcaagatcGTGACTGGAGTTCAGACGTGT |
| SEQ ID NO: 62 | CAAGCAGAAGACGGCATACGAGATgctatcctGTGACTGGAGTTCAGACGTGT |
| SEQ ID NO: 63 | CAAGCAGAAGACGGCATACGAGATtacgctacGTGACTGGAGTTCAGACGTGT |
| SEQ ID NO: 64 | CAAGCAGAAGACGGCATACGAGATtggactctGTGACTGGAGTTCAGACGTGT |
| SEQ ID NO: 65 | CAAGCAGAAGACGGCATACGAGATagagtagcGTGACTGGAGTTCAGACGTGT |
| SEQ ID NO: 66 | CAAGCAGAAGACGGCATACGAGATatccagagGTGACTGGAGTTCAGACGTGT |
| SEQ ID NO: 67 | CAAGCAGAAGACGGCATACGAGATgacgatctGTGACTGGAGTTCAGACGTGT |
| SEQ ID NO: 68 | CAAGCAGAAGACGGCATACGAGATaactgagcGTGACTGGAGTTCAGACGTGT |
| SEQ ID NO: 69 | CAAGCAGAAGACGGCATACGAGATcttaggacGTGACTGGAGTTCAGACGTGT |
| SEQ ID NO: 70 | CAAGCAGAAGACGGCATACGAGATgtgccataGTGACTGGAGTTCAGACGTGT |
| SEQ ID NO: 71 | CAAGCAGAAGACGGCATACGAGATgaatccgaGTGACTGGAGTTCAGACGTGT |
| SEQ ID NO: 72 | CAAGCAGAAGACGGCATACGAGATtcgctgttGTGACTGGAGTTCAGACGTGT |
| SEQ ID NO: 73 | CAAGCAGAAGACGGCATACGAGATttcgttggGTGACTGGAGTTCAGACGTGT |
| SEQ ID NO: 74 | CAAGCAGAAGACGGCATACGAGATaagcactgGTGACTGGAGTTCAGACGTGT |

Duplex CSD P5 Barcoded PCR Primers

| | |
|---|---|
| SEQ ID NO: 75 | AATGATACGGCGACCACCGAGATCTACACctgatcgtACACTCTTTCCCTACACGAC |
| SEQ ID NO: 76 | AATGATACGGCGACCACCGAGATCTACACactctcgaACACTCTTTCCCTACACGAC |
| SEQ ID NO: 77 | AATGATACGGCGACCACCGAGATCTACACtgagctagACACTCTTTCCCTACACGAC |
| SEQ ID NO: 78 | AATGATACGGCGACCACCGAGATCTACACgagacgatACACTCTTTCCCTACACGAC |
| SEQ ID NO: 79 | AATGATACGGCGACCACCGAGATCTACACcttgtcgaACACTCTTTCCCTACACGAC |
| SEQ ID NO: 80 | AATGATACGGCGACCACCGAGATCTACACttccaaggACACTCTTTCCCTACACGAC |
| SEQ ID NO: 81 | AATGATACGGCGACCACCGAGATCTACACcgcatgatACACTCTTTCCCTACACGAC |
| SEQ ID NO: 82 | AATGATACGGCGACCACCGAGATCTACACacggaacaACACTCTTTCCCTACACGAC |
| SEQ ID NO: 83 | AATGATACGGCGACCACCGAGATCTACACcggctaatACACTCTTTCCCTACACGAC |
| SEQ ID NO: 84 | AATGATACGGCGACCACCGAGATCTACACatcgatcgACACTCTTTCCCTACACGAC |
| SEQ ID NO: 85 | AATGATACGGCGACCACCGAGATCTACACgcaagatcACACTCTTTCCCTACACGAC |
| SEQ ID NO: 86 | AATGATACGGCGACCACCGAGATCTACACgctatcctACACTCTTTCCCTACACGAC |
| SEQ ID NO: 87 | AATGATACGGCGACCACCGAGATCTACACtacgctacACACTCTTTCCCTACACGAC |
| SEQ ID NO: 88 | AATGATACGGCGACCACCGAGATCTACACtggactctACACTCTTTCCCTACACGAC |

TABLE 1-continued

Sequences

SEQ ID NO: 89  AATGATACGGCGACCACCGAGATCTACACagagtagcACACTCTITCCCTACACGAC

SEQ ID NO: 90  AATGATACGGCGACCACCGAGATCTACACatccagagACACTCTITCCCTACACGAC

SEQ ID NO: 91  AATGATACGGCGACCACCGAGATCTACACgacgatctACACTCTITCCCTACACGAC

SEQ ID NO: 92  AATGATACGGCGACCACCGAGATCTACACaactgagcACACTCTITCCCTACACGAC

SEQ ID NO: 93  AATGATACGGCGACCACCGAGATCTACACcttaggacACACTCTITCCCTACACGAC

SEQ ID NO: 94  AATGATACGGCGACCACCGAGATCTACACgtgccataACACTCTITCCCTACACGAC

SEQ ID NO: 95  AATGATACGGCGACCACCGAGATCTACACgaatccgaACACTCTITCCCTACACGAC

SEQ ID NO: 96  AATGATACGGCGACCACCGAGATCTACACtcgctgttACACTCTITCCCTACACGAC

SEQ ID NO: 97  AATGATACGGCGACCACCGAGATCTACACttcgttggACACTCTITCCCTACACGAC

SEQ ID NO: 98  AATGATACGGCGACCACCGAGATCTACACaagcactgACACTCTITCCCTACACGAC

/5Phos/ = phosphorylated at 5'
N = degenerate bases
/5rApp/ = pre-adenylated at 5'
/3SpC3/ = 3' C3 blocking group
/3ddA/,/3ddT/,/3ddC/ and /3ddG/ = 3' dideoxy residues
Lowercase letters = sample barcode sequence
Boldface letters = UMI sequence

TABLE 2

Sensitivity and Positive Predictive Values for Variant
Calls using CSD or Kapa Prepared Libraries

| | Amount of Sample DNA Input | | | |
|---|---|---|---|---|
| | 20 ng | | 10 ng | |
| | Method of Library Preparation | | | |
| | CSD | Kapa | CSD | Kapa |
| True Positives | 277 | 248 | 267 | 242 |
| False Negatives | 14 | 43 | 24 | 49 |
| False Positives | 0 | 3 | 0 | 0 |
| Sensitivity | 0.95 | 0.85 | 0.92 | 0.83 |
| Positive Predictive Value | 1 | 0.99 | 1 | 1 |

Example 10

Four separate inputs were used to prepare libraries in triplicate. 25 ng, 50 ng, 100 ng or 200 ng of FFPE DNA were used as DNA input. The target DNA was subjected to end-repair, which included phosphorylation of the 5' ends with T4 Polynucleotide Kinase (PNK), for 30 minutes, followed by purification via 2.5× AMPure beads. The first ligation treatment P7 adapters (SEQ ID NOs:11-16), hybridized to truncated, 3' ddN blocked oligonucleotides (SEQ ID NO:17), were ligated onto the end repaired target fragments via blunt end ligation using the mutant K159S T4 DNA ligase for 15 minutes, followed by a 15 minute heat kill step. P5 adapters (SEQ ID NO:1 or SEQ ID NO:2) were annealed to the ligated first adapter at its complementary stem sequence, leaving a gap which spans the tag sequence. The gap is then filled in with a polymerase, creating an in situ UMI which is complementary to the first UMI. After the fill in step, the 3' end of the newly created in situ UMI is ligated on to the 5' end of the target fragment with Taq DNA ligase for 15 minutes. The ligated product was purified using 2.5× PEG/NaCl.

For the NGS treatment, libraries were prepared as per manufacturer's instructions. The 25 ng library was then subjected to a PCR-amplification with primers that contain sequences that are complimentary to the P5 and P7 adapters under the following conditions: 98° C. for 45 seconds, 10 cycles of: 98° C. 15 s, 60° C. for 30 seconds, 72° C. for 30 seconds, 72° C. for 1 minute, 4° C. hold. The 50 ng library was then subjected to a PCR-amplification with primers that contain sequences that are complimentary to the P5 and P7 adapters under the following conditions: 98° C. for 45 seconds, 9 cycles of: 98° C. 15 s, 60° C. for 30 seconds, 72° C. for 30 seconds, 72° C. for 1 minute, 4° C. hold. The 100 ng library was then subjected to a PCR-amplification with primers that contain sequences that are complimentary to the P5 and P7 adapters under the following conditions: 98° C. for 45 seconds, 8 cycles of: 98° C. 15 s, 60° C. for 30 seconds, 72° C. for 30 seconds, 72° C. for 1 minute, 4° C. hold. The 250 ng library was then subjected to a PCR-amplification with primers that contain sequences that are complimentary to the P5 and P7 adapters under the following conditions: 98° C. for 45 seconds, 7 cycles of: 98° C. 15 s, 60° C. for 30 seconds, 72° C. for 30 seconds, 72° C. for 1 minute, 4° C. hold.

After library preparation 500 ng of each prepared library was taken through singleplex capture using the SampleID285 panel and samples were sequenced on a NextSeq and subsampled to 16M, 36M, 60M, and 14M reads respectively. For each given input, at a similar sub-sampling level, the samples had similar on-target rates (>90%). However, the libraries obtained from CSD (LOTUS) had a lower duplication percentage as compared to Kapa, indicating a more complex library preparation. (FIG. 11).

Figure 12:
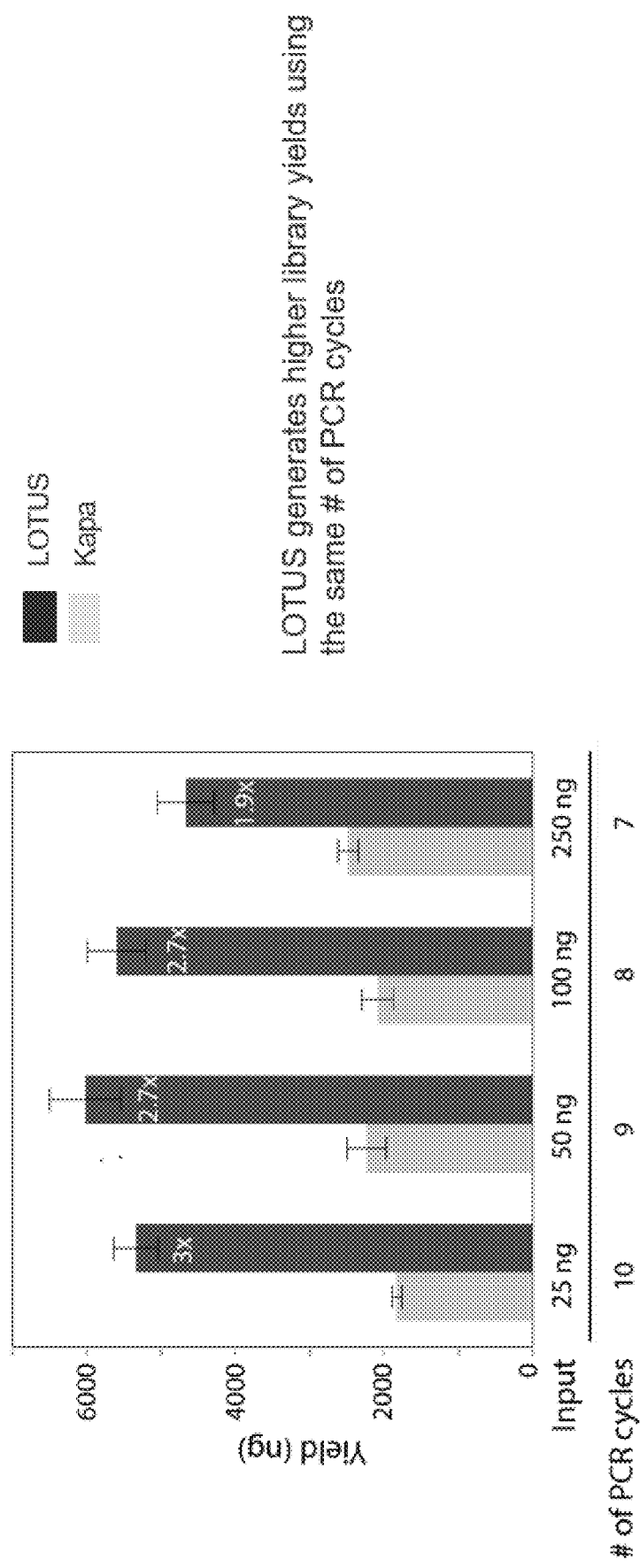
FIG. 12 is a graph showing the library yield post PCR (pre-capture). The yield of FFPE sample DNA input of CSD (LOTUS) has a higher coverage than a library prepared with an alternative capture method (Kapa). The library yields across all four input concentrations generating higher library yields using the same number of PCR cycles.

Library Yields was determined for the corresponding prepared libraries using FFPE DNA as input DNA. The library yields of CSD (LOTUS) across all four input concentrations generate higher library yields using the same number of PCR cycles compared with the KAPA method. At an FFPE DNA input concentration of 25 ng CSD (LOTUS) yielded three times (3×) more prepared library. (FIG. 12). At an FFPE DNA input concentration of 50 ng CSD (LOTUS) yielded 2.7 times (2.7×) more prepared library. (FIG. 12). At an FFPE DNA input concentration of 100 ng CSD (LOTUS) yieleded 2.7 times (2.7×) more prepared library. (FIG. 12). At an FFPE DNA input concentration of 250 ng CSD (LOTUS) yielded 1.9 times (1.9×) more prepared library. (FIG. 12).

Figure 13:
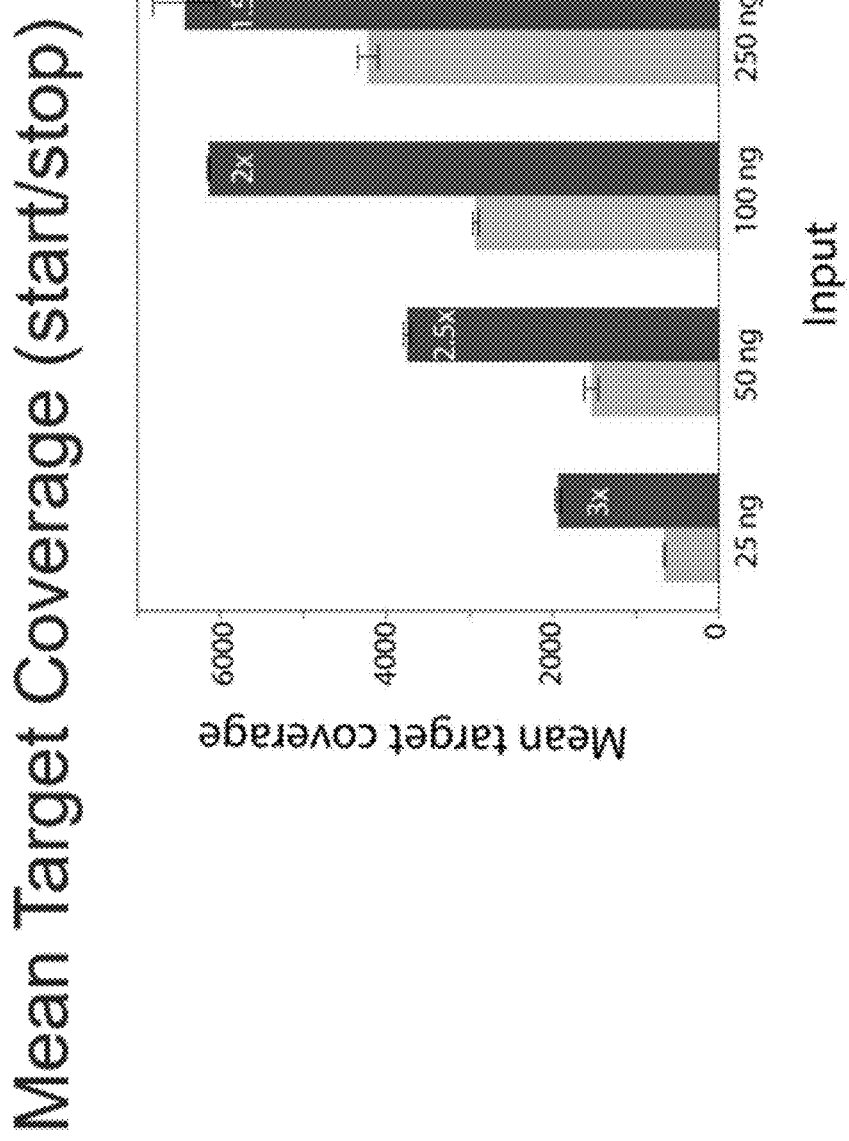
FIG. 13 is a graph showing mean target coverage by start/stop deduplication. Libraries prepared from FFPE sample DNA using CSD (LOTUS) have a higher mean target coverage.
Figure 17:
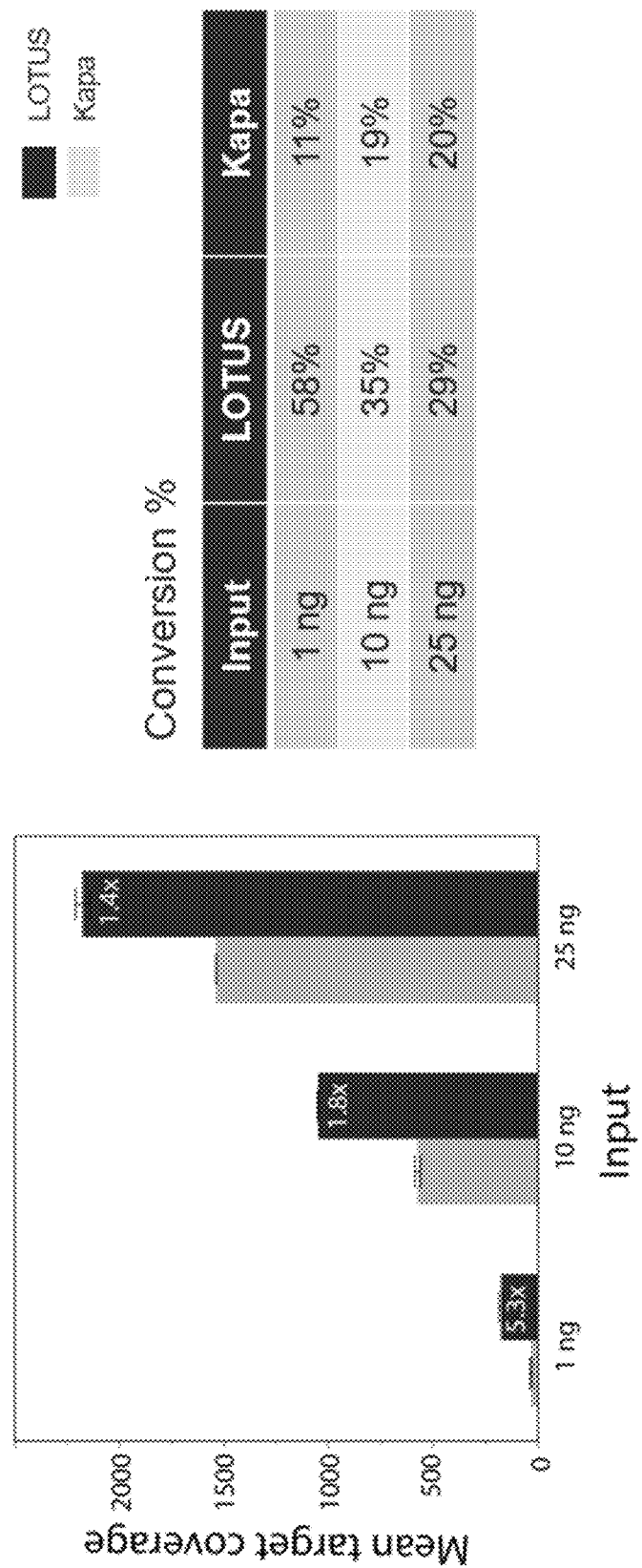
FIG. 17 is a graph showing the mean target coverage by start/stop deduplication. Libraries prepared from sample cfDNA using the present invention have a higher mean target coverage indicating that the library has converted more input molecules into a quenchable library which also indicates the ability to increase sensitivity for detecting variants in the sequenced library.

Mean Target Coverage by start/start deduplication was determined for the corresponding prepared libraries using FFPE DNA as input DNA. (FIG. 13). CSD (LOTUS) converts 3× more input molecules at 25 ng FFPE DNA input, 2.5× more input molecules at 50 ng FFPE DNA input, 2× more input at 100 ng FFPE DNA input, and 1.5× more input molecules at 250 ng FFPE DNA input. (FIG. 17). The mean target coverage across all four FFPE DNA input concentrations generate higher mean target coverage in the CSD (LOTUS) method as compared to KAPA. This indicates that CSD (LOTUS,) at each FFPE DNA input concentration, prepared libraries have converted more input molecules into a sequencable library. This increased conversion also indicates the ability to increase sensitivity for detecting variants in the sequenced library.

Figure 14:
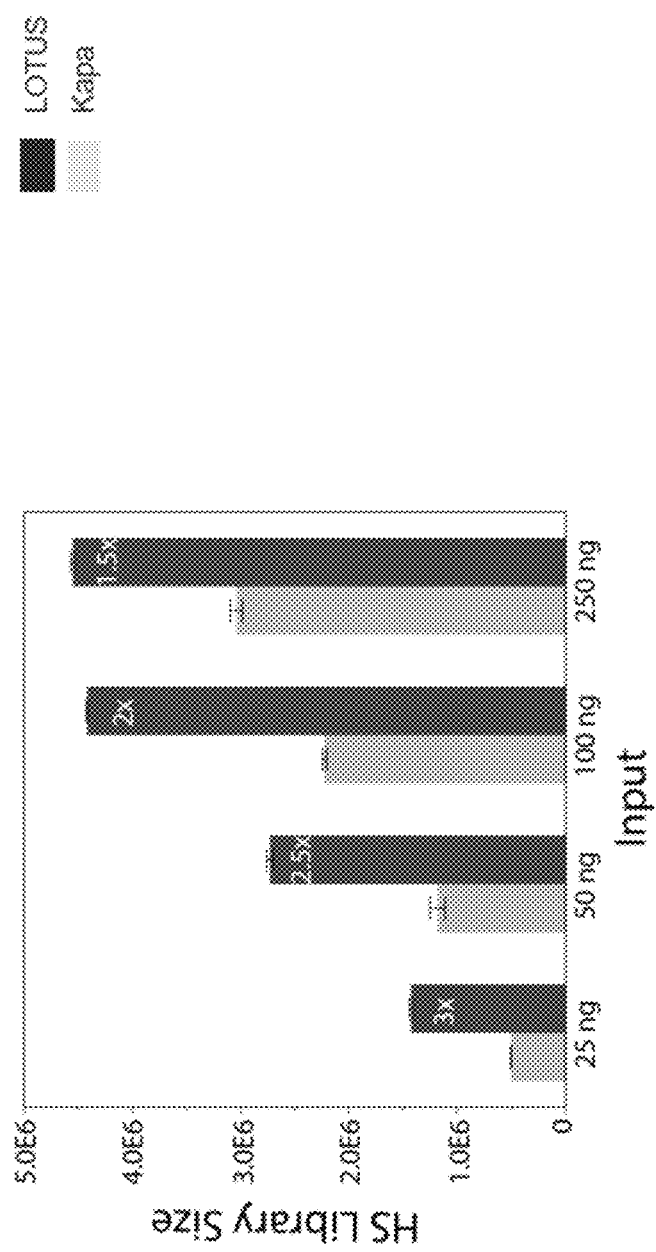
FIG. 14 is a graph showing the complexity as measured by HS library size of a library prepared from FFPE sample DNA. The FIG. illustrates that libraries prepared by the present invention generate a higher number of unique molecules.

HS library size was determined for the corresponding libraries using FFPE DNA as target input DNA. (FIG. 14). The HS library size across all four FFPE DNA input concentrations generate a higher number of unique molecules in the CSD (LOTUS) method as compared to KAPA.

Example 11

Three separate libraries of cfDNA were prepared with each input prepared in triplicate. 1 ng, 10 ng, and 25 ng of cfDNA were used as DNA input. The DNA was subjected to end-repair, which included phosphorylation of the 5' ends with T4 Polynucleotide Kinase (PNK), for 30 minutes, followed by purification via 2.5× AMPure beads. The first ligation treatment P7 adapters (SEQ ID NOs:11-16), hybridized to truncated, 3' ddN blocked oligonucleotides (SEQ ID NO:17), were ligated onto the end repaired target fragments via blunt end ligation using the mutant K159S T4 DNA ligase for 15 minutes, followed by a 15 minute heat kill step. P5 adapters (SEQ ID NO:1 or SEQ ID NO:2) were annealed to the ligated first adapter at its complementary stem sequence, leaving a gap which spans the tag sequence. The gap is then filled in with a polymerase, creating an in situ UMI which is complementary to the first UMI. After the fill in step, the 3' end of the newly created in situ UMI is ligated on to the 5' end of the target fragment with Taq DNA ligase for 15 minutes. The ligated product was purified using 2.5× PEG/NaCl.

The 1 ng library was then subjected to a PCR-amplification with primers that contain sequences that are complimentary to the P5 and P7 adapters under the following conditions: 98° C. for 45 seconds, 12 cycles of: 98° C. 15 s, 60° C. for 30 seconds, 72° C. for 30 seconds, 72° C. for 1 minute, 4° C. hold. The 10 ng library was then subjected to a PCR-amplification with primers that contain sequences that are complimentary to the P5 and P7 adapters under the following conditions: 98° C. for 45 seconds, 10 cycles of: 98° C. 15 s, 60° C. for 30 seconds, 72° C. for 30 seconds, 72° C. for 1 minute, 4° C. hold. The 25 ng library was then subjected to a PCR-amplification with primers that contain sequences that are complimentary to the P5 and P7 adapters under the following conditions: 98° C. for 45 seconds, 8 cycles of: 98° C. 15 s, 60° C. for 30 seconds, 72° C. for 30 seconds, 72° C. for 1 minute, 4° C. hold.

After library preparation 500 ng of each prepared library (except for Kapa 1 ng libraries in which 190 ng was taken into the downstream capture methods as 500 ng of library could not be generated) was taken through singleplex capture using the SampleID285 panel and samples were sequenced on a NextSeq and subsampled to 12M, 28M, and 90M reads respectively. For each given input, at a similar sub-sampling level, the samples had similar on-target rates (>90%). However, the libraries obtained from CSD (LOTUS) had a lower duplication percentage as compared to Kapa, indicating a more complex library preparation. (FIG. 15).

Figure 16:
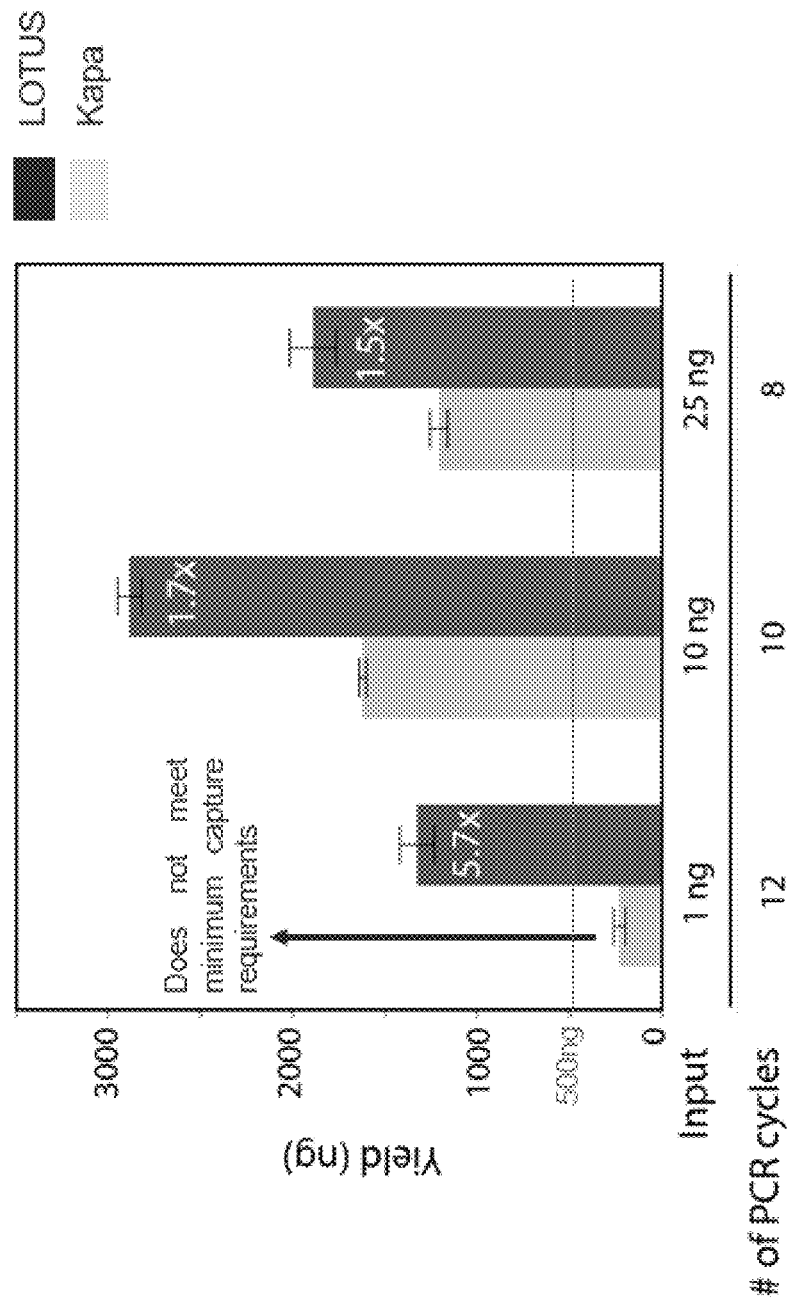
FIG. 16 is a graph showing the library yield post PCR (pre-capture). The yield of cfDNA of CSD (LOTUS) has a higher coverage than a library prepared with an alternative capture method (Kapa). The library yield of CSD (LOTUS) across all three input concentrations generates higher library yields using the same number of PCR cycles.

Library Yields was determined for the corresponding prepared libraries using FFPE DNA as input DNA. The library yields of CSD (LOTUS) across all three cfDNA input concentrations generate higher library yields using the same number of PCR cycles compared with the KAPA method. At an cfDNA input concentration of 1 ng CSD (LOTUS) yielded 5.7 times (5.7×) more prepared library. (FIG. 16). Additionally, the 1 ng input sample demonstrates the unique ability of CSD (LOTUS) to generate sufficient library quantities for downstream capture applications. At an cfDNA input concentration of 10 ng CSD (LOTUS) yielded 1.7 times (1.7×) more prepared library. (FIG. 16). At an cfDNA input concentration of 25 ng CSD (LOTUS) yielded 1.5 times (1.5×) more prepared library. (FIG. 16).

Mean Target Coverage by start/start deduplication was determined for the corresponding prepared libraries using cfDNA as target input DNA. (FIG. 17). CSD (LOTUS) coverts 5.3× more input molecules at 1 ng cfDNA input, 1.8× more input molecules at 10 ng cfDNA input, and 1.4× input molecules at 25 ng cfDNA input. (FIG. 17). The mean target coverage across all three cfDNA input concentrations generate higher mean target coverage in the CSD (LOTUS) method as compared to KAPA. This increase in mean target coverage indicates that CSD (LOTUS) prepared libraries have converted more input molecules into a sequencable library. This increased conversion also indicates the ability to increase sensitivity for detecting variants in the sequenced library.

Figure 18:
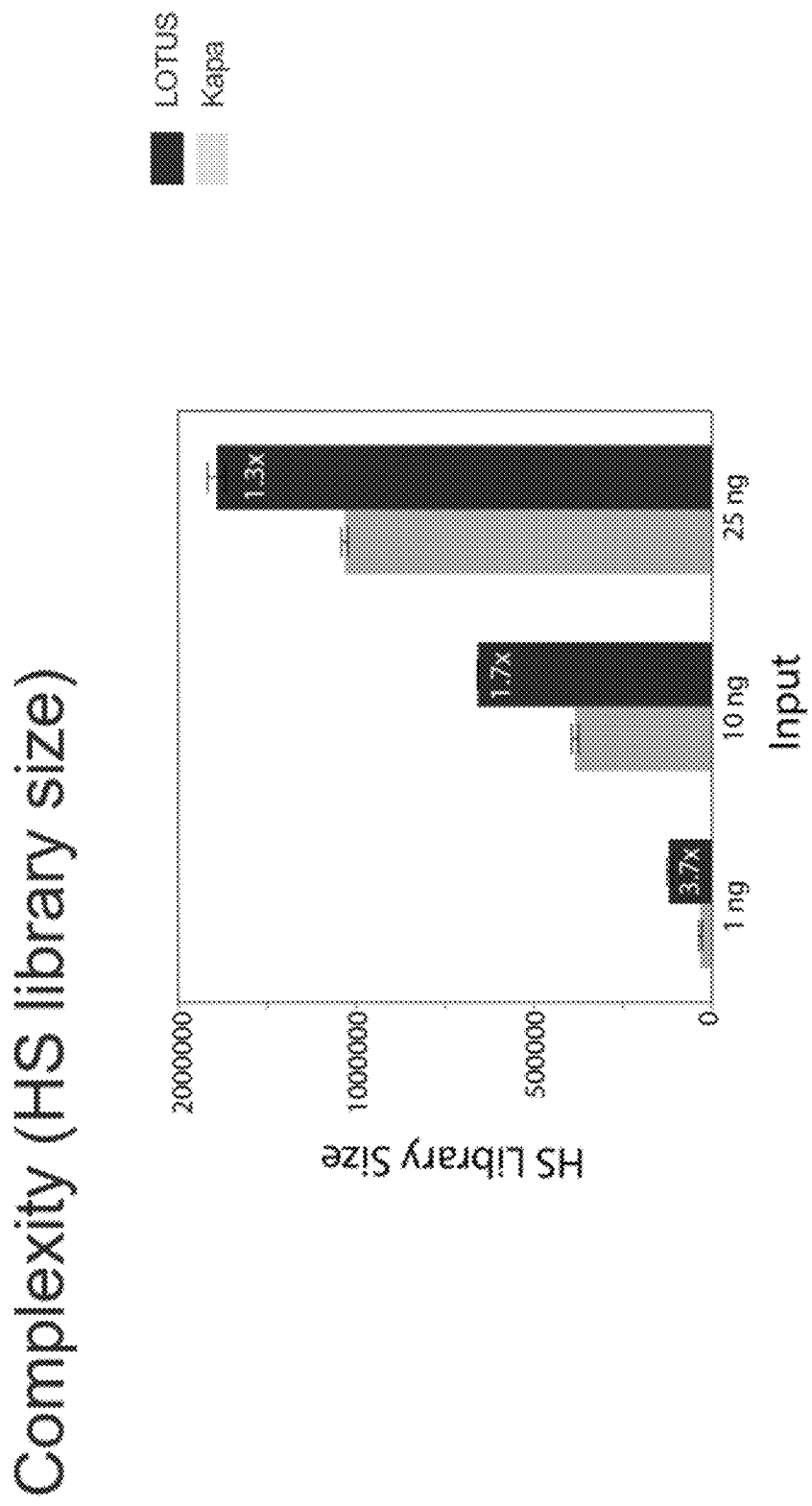
FIG. 18 is a graph showing the complexity as measured by HS library size of a library prepared from FFPE sample DNA. The FIG. illustrates that libraries prepared by the present invention generate a higher number of unique molecules as compared to an alternative library preparation method.
Figure 19A:
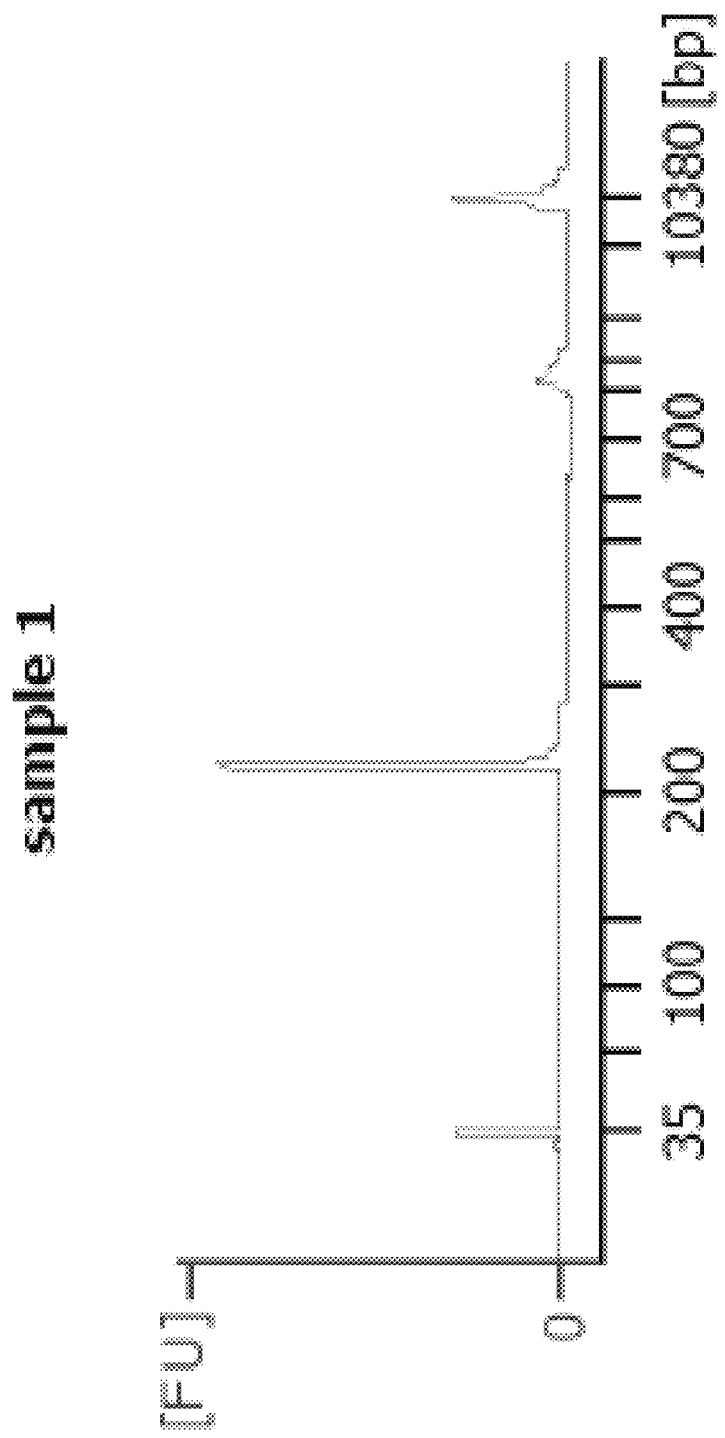
FIGS. 19A, 19B, 19C, 19D, 19E, 19F, and 19G are Bioanalzyer traces for the ligation steps of the present invention. Sample 1 is the starting unligated gBlocks Gene Fragment. Samples 2 to 4 are the product of the first ligation performed in triplicate. Samples 5-7 are the product of the second ligation performed in triplicate.
Figure 19B:
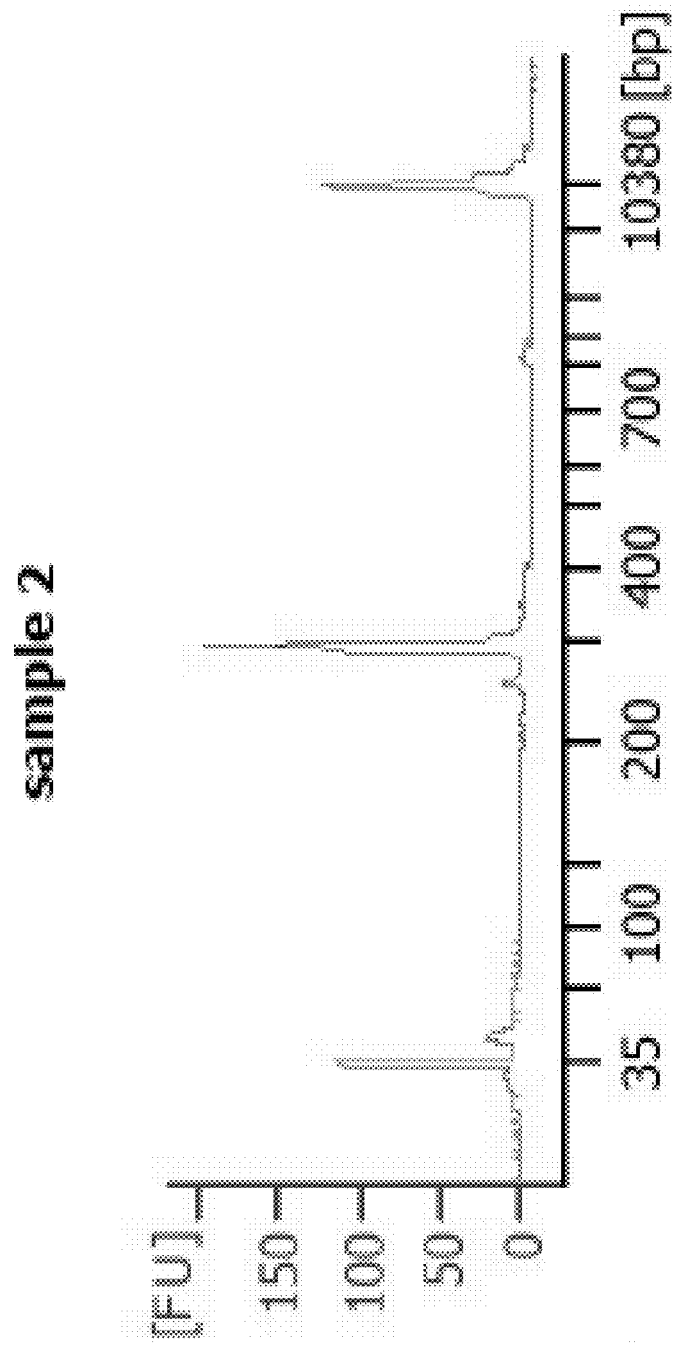
Figure 19C:
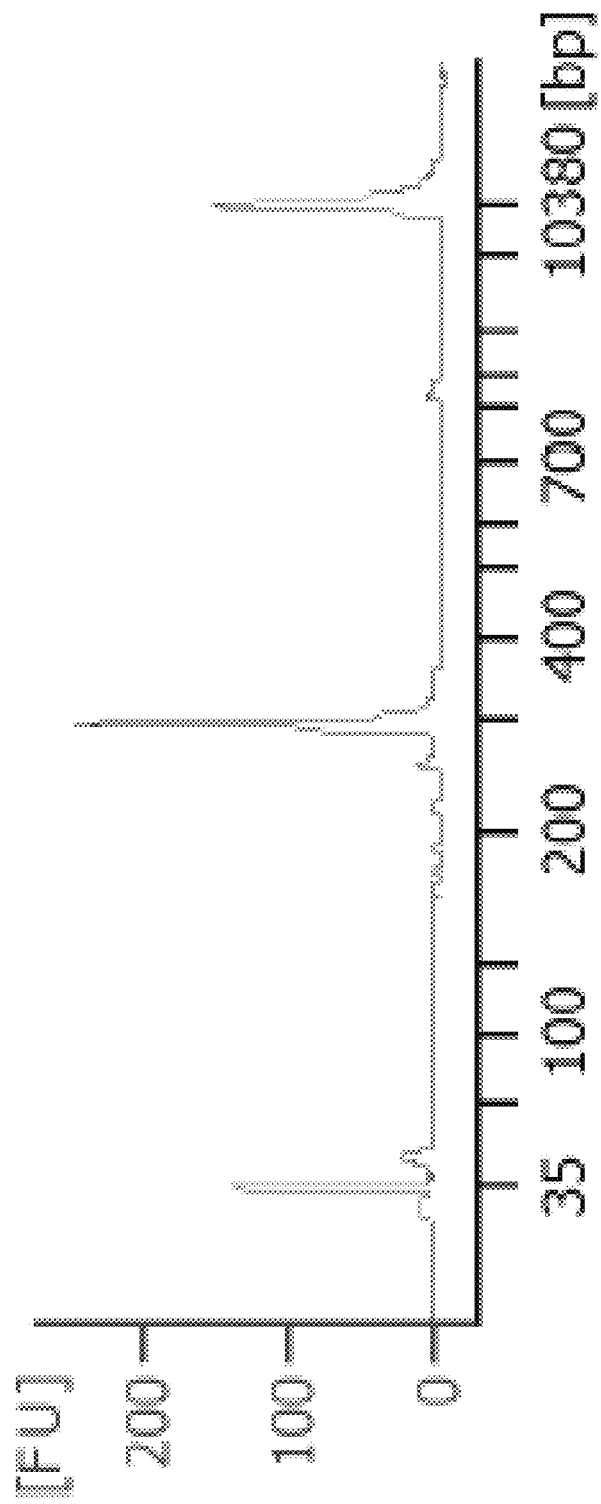
Figure 19D:
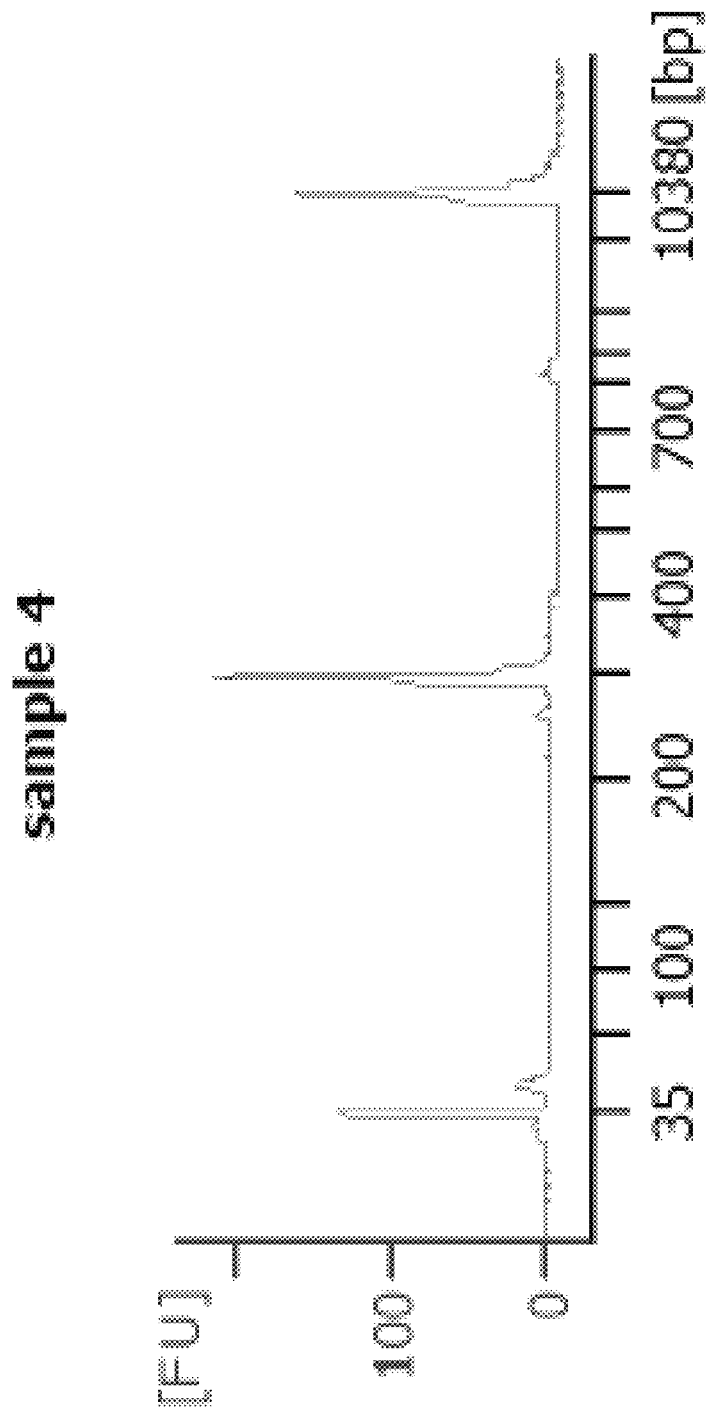
Figure 19E:
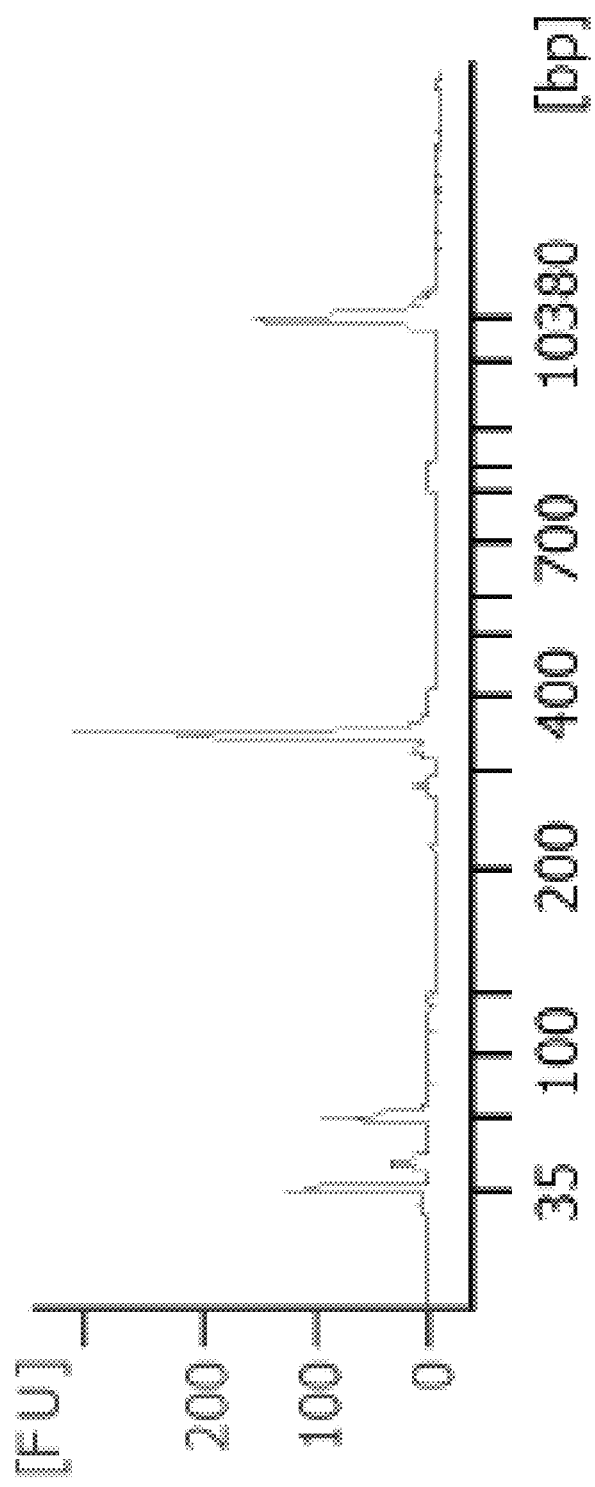
Figure 19F:
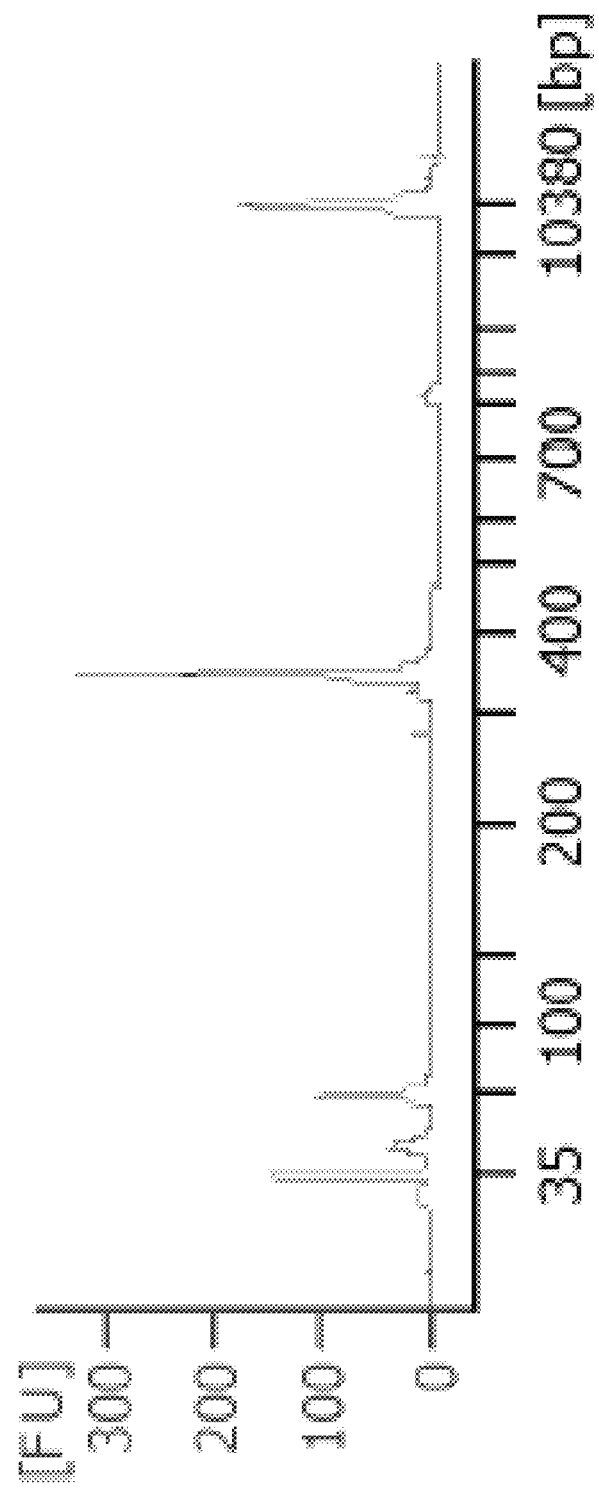
Figure 19G:
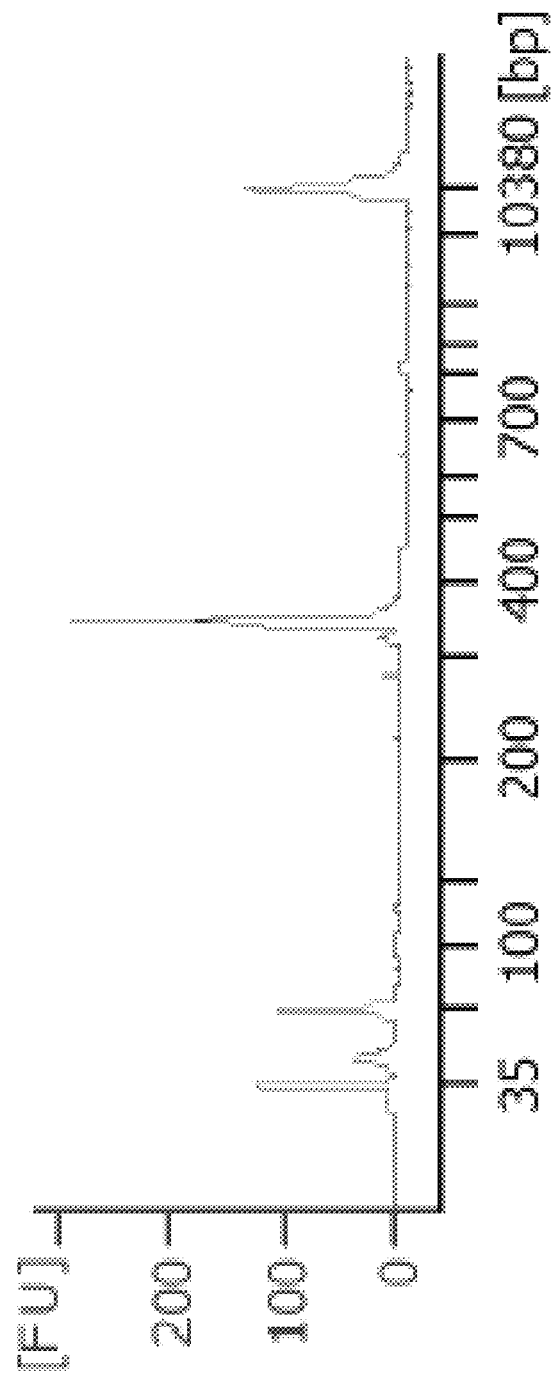

HS library size was determined for the corresponding libraries using cfDNA as target input DNA. (FIG. 18). The HS library size across all three cfDNA input concentrations generate a higher number of unique molecules in the CSD (LOTUS) method as compared to KAPA.

Example 12

10 ng of gBlocks Gene fragments were subjected to end-repair, which included phosphorylation of the 5' ends with T4 Polynucleotide Kinase (PNK), for 30 minutes, followed by purification via 2.5× AMPure beads. The first ligation treatment P7 adapters (SEQ ID NOs:11-16), hybridized to truncated, 3' ddN blocked oligonucleotides (SEQ ID NO:17), were ligated onto the end repaired target fragments via blunt end ligation using the mutant K159S T4 DNA ligase for 15 minutes, followed by a 15 minute heat kill step. P5 adapters (SEQ ID NO:1 or SEQ ID NO:2) were then ligated onto the first ligation product using Taq DNA ligase for 30 minutes, followed by purification using 2× PEG/NaCl solution, and eluted into 20 ul elution buffer. To look at the product after 1$^{st}$ ligation, no second ligation was performed and reaction mixtures were directly subject to 2× PEG/NaCl purification. 1 ul gBlocks Gene Fragments, 1 ul of the eluted first ligation product solution, 1 ul of the eluted second ligation product solution were analyzed on an Agilent Bioanalyzer following the manufacturer's instructions.

The Bioanalyzer traces (FIGS. 19A-G) shows the gBlocks Gene Fragment (sample 1), the first ligation product prepared in triplicate (Sample 2, Sample 3, and Sample 4), and the second ligation product prepared in triplicate (Sample 5, Sample 6, and Sample 7). The traces show that the combination of unique adapters structure and use of the mutant ligates enables increased ligation efficiency.

Figure 20:
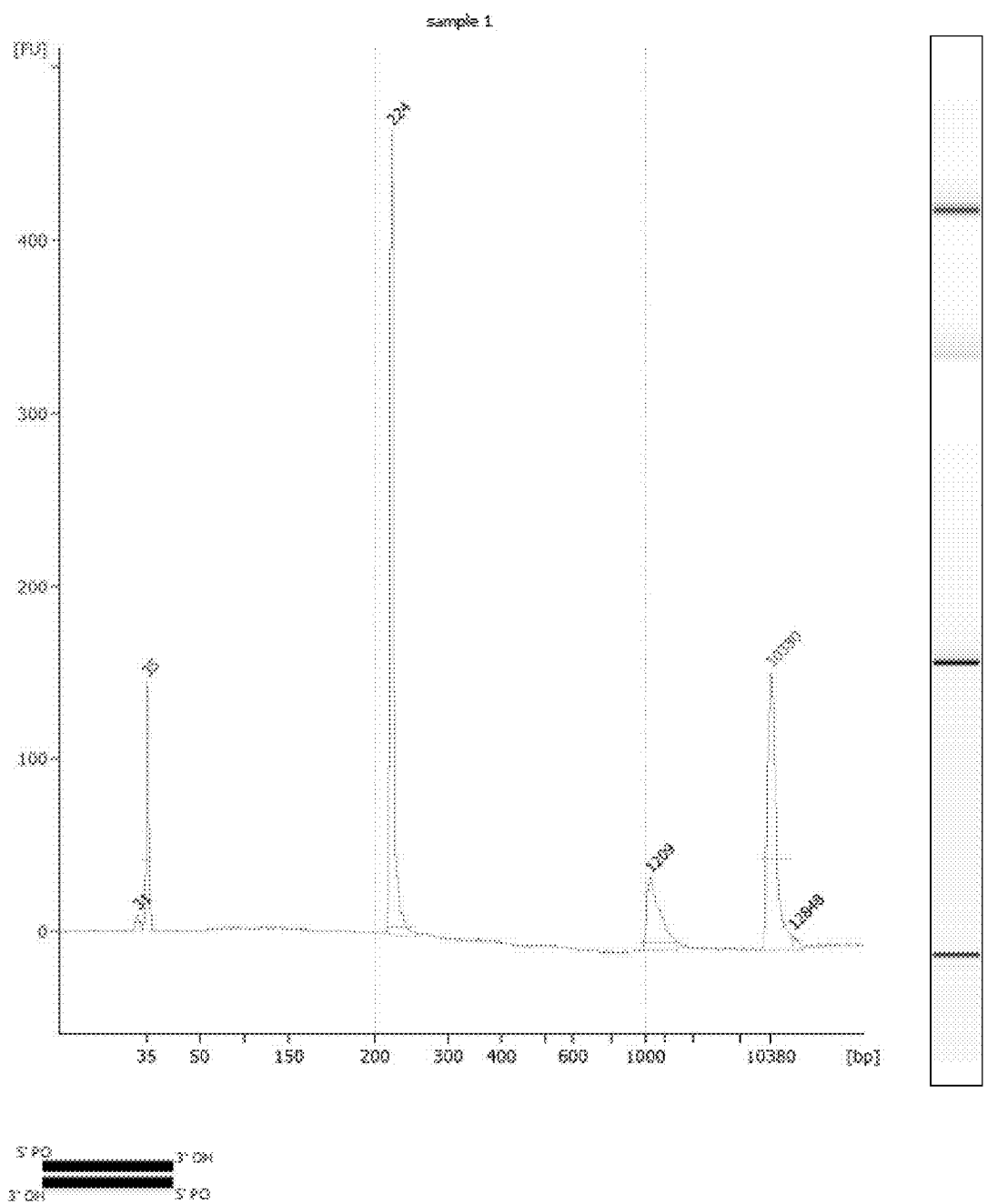
FIG. 20 is a Bioanalzyer trace of a gBlocks Gene Fragment prior to the ligation of any adapters.

The starting unligated gBlocks Gene Fragment is a double stranded DNA fragment in which both ends are phosphorylated (FIG. 20). The Bioanalyzer trace shows the expected gBlocks Gene Fragment length of 224 base pairs prior to any ligation event (FIG. 20).

Figure 21:
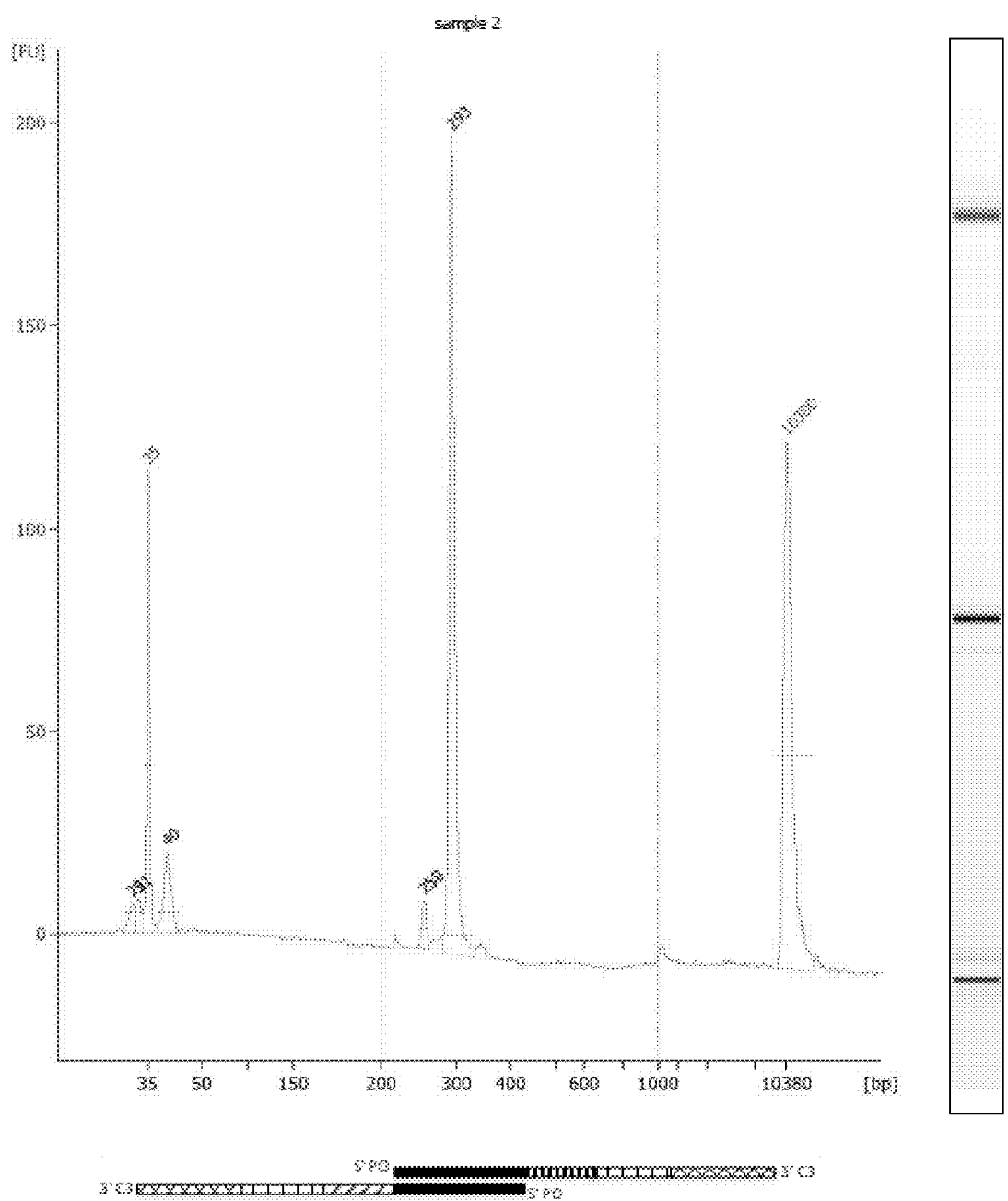
FIG. 21 is a Bioanalzyer trace of a gBlocks Gene Fragment following ligation of a first adapter.

Following the ligation of the first adapter to the starting duplex gBlocks Gene Fragment the ligated product was analyzed on a Bioanalzyer. The Bioanalzyer trace shows the expected first ligation product length of 293 base pairs and the coversion of unligated gBlocks Gene Fragment to ligated product (FIG. 21).

Figure 22:
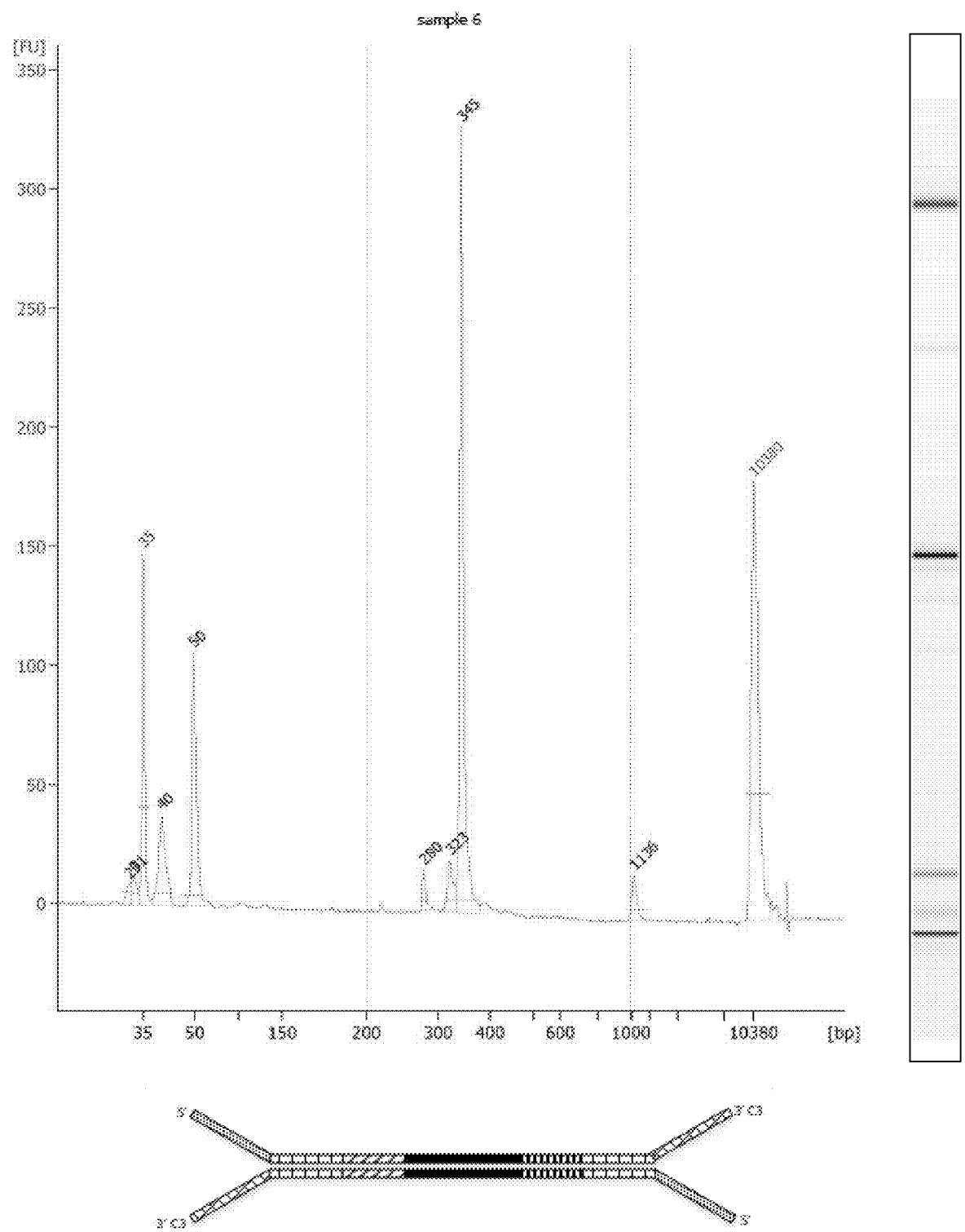
FIG. 22 is a Bioanalzyer trace of a fully ligated gBlocks Gene Fragment having adapters ligated to both ends.
Figure 22:
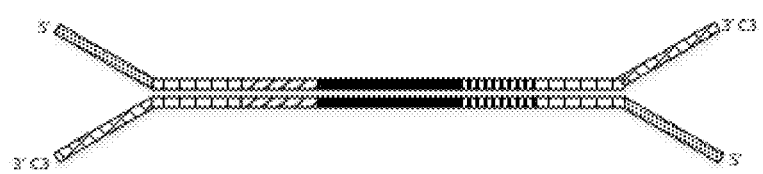

Following the ligation of the second adapter to the first ligation product the second ligation product was analyzed on a Bioanalzyer. The Bioanalzyer trace shows the expected product length of 345 base pairs and the conversion of singly ligated product to fully ligated product in which the fully ligated product has NGS adapters ligated to both ends of each strand of the target nucleic acid molecule (FIG. 22).

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

For reasons of completeness, various aspects of the invention are set out in the following numbered clauses:

Clause 1: A sequencing adapter comprising:
A first DNA strand and a second DNA strand; wherein the first DNA strand has a blocking group at its 3' end and a 5' phosphate; wherein the second DNA strand has a dideoxy nucleotide base (ddN) at its 3' end; and wherein the second DNA strand is partially complementary to the first DNA strand.

Clause 2: The sequencing adapter of clause 1 wherein the dideoxy nucleotide bases is selected from a group comprising ddA, ddT, ddC, or ddG.

Clause 3: The sequencing adapter of clause 1 or clause 2 where the blocking group is a C3 spacer.

Clause 4: The sequencing adapter of any one of clauses 1-3 wherein the first DNA strand contains a first sequencing primer binding site.

Clause 5: The sequencing adapter of clause 4 wherein the first DNA strand contains a unique molecular identifier.

Clause 6: The sequencing adapter of any one of clauses 1-5, wherein the second DNA strand contains a unique molecular identifier.

Clause 7: The sequencing adapter of any one of clauses 1-6, wherein the second DNA strand is 5 to 15 bases.

Clause 8: The sequencing adapter of any one of clauses 1-7, wherein the second DNA strand is 10 bases.

Clause 9: The sequencing adapter of any one of clauses 1-8, wherein the first DNA strand is selected from the group comprising SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, or SEQ ID NO: 33.

Clause 10: The sequencing adapter of any one of clauses 1-9, wherein the second DNA strand is selected from the group comprising SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO:42, SEQ ID NO: 43, SEQ ID NO: 44, SEQ ID NO: 45, SEQ ID NO: 46, SEQ ID NO: 47, SEQ ID NO: 48, or SEQ ID NO: 49.

What is claimed is:

1. A sequencing adapter comprising:
a first DNA strand and a second DNA strand;
wherein the first DNA strand has a blocking group at its 3' end and a 5' phosphate and comprises a nucleic acid sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, and SEQ ID NO: 33;
wherein the second DNA strand has a dideoxy nucleotide base (ddN) at its 3' end and comprises a nucleic acid sequence selected from the group consisting of SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO:42, SEQ ID NO: 43, SEQ ID NO: 44, SEQ ID NO: 45, SEQ ID NO: 46, SEQ ID NO: 47, SEQ ID NO: 48, and SEQ ID NO: 49;
and wherein the second DNA strand is partially complementary to the first DNA strand.

2. The sequencing adapter of claim 1 wherein the dideoxy nucleotide base is selected from the group consisting of ddA, ddT, ddC, and ddG.

3. The sequencing adapter of claim 1 where the blocking group is a C3 spacer.

4. The sequencing adapter of claim 1 wherein the first DNA strand contains a first sequencing primer binding site.

5. The sequencing adapter of claim 4 wherein the first DNA strand contains a unique molecular identifier.

6. The sequencing adapter of claim 1, wherein the second DNA strand contains a unique molecular identifier.

7. The sequencing adapter of claim 1, wherein the second DNA strand is 5 to 15 bases in length.

8. The sequencing adapter of claim 6, wherein the second DNA strand is 10 bases in length.

* * * * *

SEQUENCE LISTING

<160> NUMBER OF SEQ ID NOS: 98

<210> SEQ ID NO 1
<211> LENGTH: 58
<212> TYPE: DNA
<213> ORGANISM: Artificial Sequence
<220> FEATURE:
<223> OTHER INFORMATION: synthetic nucleic acid

<400> SEQUENCE: 1
aatgatacgg cgaccaccga gatctacact ctttccctac acgacgctct tccgatct        58

<210> SEQ ID NO 2
<211> LENGTH: 68
<212> TYPE: DNA
<213> ORGANISM: Artificial Sequence
<220> FEATURE:
<223> OTHER INFORMATION: synthetic nucleic acid

```
<220> FEATURE:
<221> NAME/KEY: misc_feature
<222> LOCATION: (30)..(35)
<223> OTHER INFORMATION: n is a, g, c, or t

<400> SEQUENCE: 2
aatgatacgg cgaccaccga gatctacacn nnnnnacact ctttccctac acgacgctct    60
tccgatct                                                            68

<210> SEQ ID NO 3
<211> LENGTH: 70
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5Phos
<220> FEATURE:
<221> NAME/KEY: misc_feature
<222> LOCATION: (35)..(40)
<223> OTHER INFORMATION: n is a, g, c, or t

<400> SEQUENCE: 3
agatcggaag agcacacgtc tgaactccag tcacnnnnnn atcacgatct cgtatgccgt    60
cttctgcttg                                                          70

<210> SEQ ID NO 4
<211> LENGTH: 70
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5Phos
<220> FEATURE:
<221> NAME/KEY: misc_feature
<222> LOCATION: (35)..(40)
<223> OTHER INFORMATION: n is a, g, c, or t

<400> SEQUENCE: 4
agatcggaag agcacacgtc tgaactccag tcacnnnnnn cgatgtatct cgtatgccgt    60
cttctgcttg                                                          70

<210> SEQ ID NO 5
<211> LENGTH: 70
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5Phos
<220> FEATURE:
<221> NAME/KEY: misc_feature
<222> LOCATION: (35)..(40)
<223> OTHER INFORMATION: n is a, g, c, or t

<400> SEQUENCE: 5
agatcggaag agcacacgtc tgaactccag tcacnnnnnn ttaggcatct cgtatgccgt    60
cttctgcttg                                                          70

<210> SEQ ID NO 6
```

<211> LENGTH: 70
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5Phos
<220> FEATURE:
<221> NAME/KEY: misc_feature
<222> LOCATION: (35)..(40)
<223> OTHER INFORMATION: n is a, g, c, or t

<400> SEQUENCE: 6
agatcggaag agcacacgtc tgaactccag tcacnnnnnn tgaccaatct cgtatgccgt    60
cttctgcttg    70

<210> SEQ ID NO 7
<211> LENGTH: 70
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5Phos
<220> FEATURE:
<221> NAME/KEY: misc_feature
<222> LOCATION: (35)..(40)
<223> OTHER INFORMATION: n is a, g, c, or t

<400> SEQUENCE: 7
agatcggaag agcacacgtc tgaactccag tcacnnnnnn acagtgatct cgtatgccgt    60
cttctgcttg    70

<210> SEQ ID NO 8
<211> LENGTH: 70
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5Phos
<220> FEATURE:
<221> NAME/KEY: misc_feature
<222> LOCATION: (35)..(40)
<223> OTHER INFORMATION: n is a, g, c, or t

<400> SEQUENCE: 8
agatcggaag agcacacgtc tgaactccag tcacnnnnnn gccaatatct cgtatgccgt    60
cttctgcttg    70

<210> SEQ ID NO 9
<211> LENGTH: 70
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5Phos
<220> FEATURE:
<221> NAME/KEY: misc_feature
<222> LOCATION: (35)..(40)
<223> OTHER INFORMATION: n is a, g, c, or t

<400> SEQUENCE: 9
agatcggaag agcacacgtc tgaactccag tcacnnnnnn cagatcatct cgtatgccgt    60
cttctgcttg    70

<210> SEQ ID NO 10
<211> LENGTH: 70
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5Phos
<220> FEATURE:
<221> NAME/KEY: misc_feature
<222> LOCATION: (35)..(40)
<223> OTHER INFORMATION: n is a, g, c, or t

<400> SEQUENCE: 10
agatcggaag agcacacgtc tgaactccag tcacnnnnnn acttgaatct cgtatgccgt    60
cttctgcttg    70

<210> SEQ ID NO 11
<211> LENGTH: 72
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (43)..(48)
<223> OTHER INFORMATION: n is a, g, c, or t
<220> FEATURE:
<221> NAME/KEY: misc_feature
<222> LOCATION: (72)..(72)
<223> OTHER INFORMATION: 3SpC3

<400> SEQUENCE: 11
agatcggaag agcacacgtc tgaactccag tcacaacggc ggnnnnnnat ctcgtatgcc    60
gtcttctgct tg    72

<210> SEQ ID NO 12
<211> LENGTH: 72
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (43)..(48)
<223> OTHER INFORMATION: n is a, g, c, or t
<220> FEATURE:
<221> NAME/KEY: misc_feature
<222> LOCATION: (72)..(72)
<223> OTHER INFORMATION: 3SpC3

<400> SEQUENCE: 12
agatcggaag agcacacgtc tgaactccag tcaccatccg ttnnnnnnat ctcgtatgcc    60
gtcttctgct tg                                                                72

<210> SEQ ID NO 13
<211> LENGTH: 72
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (43)..(48)
<223> OTHER INFORMATION: n is a, g, c, or t
<220> FEATURE:
<221> NAME/KEY: misc_feature
<222> LOCATION: (72)..(72)
<223> OTHER INFORMATION: 3SpC3

<400> SEQUENCE: 13
agatcggaag agcacacgtc tgaactccag tcaccgaatt ggnnnnnnat ctcgtatgcc    60
gtcttctgct tg                                                                72

<210> SEQ ID NO 14
<211> LENGTH: 72
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (43)..(48)
<223> OTHER INFORMATION: n is a, g, c, or t
<220> FEATURE:
<221> NAME/KEY: misc_feature
<222> LOCATION: (72)..(72)
<223> OTHER INFORMATION: 3SpC3

<400> SEQUENCE: 14
agatcggaag agcacacgtc tgaactccag tcacttagaa ccnnnnnnat ctcgtatgcc    60
gtcttctgct tg                                                                72

<210> SEQ ID NO 15
<211> LENGTH: 72
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (43)..(48)
<223> OTHER INFORMATION: n is a, g, c, or t
<220> FEATURE:
<221> NAME/KEY: misc_feature
<222> LOCATION: (72)..(72)
<223> OTHER INFORMATION: 3SpC3

<400> SEQUENCE: 15
agatcggaag agcacacgtc tgaactccag tcacggccaa cgnnnnnnat ctcgtatgcc    60
gtcttctgct tg                                                                72

<210> SEQ ID NO 16
<211> LENGTH: 72
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (43)..(48)
<223> OTHER INFORMATION: n is a, g, c, or t
<220> FEATURE:
<221> NAME/KEY: misc_feature
<222> LOCATION: (72)..(72)
<223> OTHER INFORMATION: 3SpC3

<400> SEQUENCE: 16
agatcggaag agcacacgtc tgaactccag tcactcttgg ttnnnnnnat ctcgtatgcc    60
gtcttctgct tg    72

<210> SEQ ID NO 17
<211> LENGTH: 12
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (12)..(12)
<223> OTHER INFORMATION: ddT

<400> SEQUENCE: 17
ctcttccgat ct    12

<210> SEQ ID NO 18
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 18
acgatcagag atcggaagag cacacgtctg aactccagtc ac    42

<210> SEQ ID NO 19
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:

<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 19
tcgagagtag atcggaagag cacacgtctg aactccagtc ac        42

<210> SEQ ID NO 20
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 20
ctagctcaag atcggaagag cacacgtctg aactccagtc ac        42

<210> SEQ ID NO 21
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 21
atcgtctcag atcggaagag cacacgtctg aactccagtc ac        42

<210> SEQ ID NO 22
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

```
<400> SEQUENCE: 22
tcgacaagag atcggaagag cacacgtctg aactccagtc ac                         42

<210> SEQ ID NO 23
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 23
ccttggaaag atcggaagag cacacgtctg aactccagtc ac                         42

<210> SEQ ID NO 24
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 24
atcatgcgag atcggaagag cacacgtctg aactccagtc ac                         42

<210> SEQ ID NO 25
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 25
tgttccgtag atcggaagag cacacgtctg aactccagtc ac                         42

<210> SEQ ID NO 26
```

```
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 26
attagccgag atcggaagag cacacgtctg aactccagtc ac                          42

<210> SEQ ID NO 27
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 27
cgatcgatag atcggaagag cacacgtctg aactccagtc ac                          42

<210> SEQ ID NO 28
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 28
gatcttgcag atcggaagag cacacgtctg aactccagtc ac                          42

<210> SEQ ID NO 29
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
```

```
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 29
aggatagcag atcggaagag cacacgtctg aactccagtc ac                              42

<210> SEQ ID NO 30
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 30
gtagcgtaag atcggaagag cacacgtctg aactccagtc ac                              42

<210> SEQ ID NO 31
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 31
agagtccaag atcggaagag cacacgtctg aactccagtc ac                              42

<210> SEQ ID NO 32
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
```

```
<221> NAME/KEY: misc_feature
<222> LOCATION: (42)..(42)
<223> OTHER INFORMATION: 3SpC3

<400> SEQUENCE: 32
gctactctag atcggaagag cacacgtctg aactccagtc ac                        42

<210> SEQ ID NO 33
<211> LENGTH: 42
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (1)..(1)
<223> OTHER INFORMATION: 5rApp
<220> FEATURE:
<221> NAME/KEY: misc_feature
<222> LOCATION: (1)..(8)
<223> OTHER INFORMATION: UMI
<220> FEATURE:
<221> NAME/KEY: misc_feature
<222> LOCATION: (42)..(42)
<223> OTHER INFORMATION: 3SpC3

<400> SEQUENCE: 33
ctctggatag atcggaagag cacacgtctg aactccagtc ac                        42

<210> SEQ ID NO 34
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddT

<400> SEQUENCE: 34
ctctgatcgt                                                            10

<210> SEQ ID NO 35
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddA

<400> SEQUENCE: 35
ctactctcga                                                            10

<210> SEQ ID NO 36
<211> LENGTH: 10
<212> TYPE: DNA
<213> ORGANISM: Artificial Sequence
<220> FEATURE:
<223> OTHER INFORMATION: synthetic nucleic acid
```

-continued

```
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddG

<400> SEQUENCE: 36
cttgagctag                                                                10

<210> SEQ ID NO 37
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddT

<400> SEQUENCE: 37
ctgagacgat                                                                10

<210> SEQ ID NO 38
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddA

<400> SEQUENCE: 38
ctcttgtcga                                                                10

<210> SEQ ID NO 39
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddG

<400> SEQUENCE: 39
ctttccaagg                                                                10

<210> SEQ ID NO 40
<211> LENGTH: 10
<212> TYPE: DNA
<213> ORGANISM: Artificial Sequence
<220> FEATURE:
```

```
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddT

<400> SEQUENCE: 40
ctcgcatgat                                                                10

<210> SEQ ID NO 41
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddA

<400> SEQUENCE: 41
ctacggaaca                                                                10

<210> SEQ ID NO 42
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddT

<400> SEQUENCE: 42
ctcggctaat                                                                10

<210> SEQ ID NO 43
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddG

<400> SEQUENCE: 43
ctatcgatcg                                                                10

<210> SEQ ID NO 44
<211> LENGTH: 10
<212> TYPE: DNA
<213> ORGANISM: Artificial Sequence
```

```
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddC

<400> SEQUENCE: 44
ctgcaagatc                                                          10

<210> SEQ ID NO 45
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddT

<400> SEQUENCE: 45
ctgctatcct                                                          10

<210> SEQ ID NO 46
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddC

<400> SEQUENCE: 46
cttacgctac                                                          10

<210> SEQ ID NO 47
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddT

<400> SEQUENCE: 47
cttggactct                                                          10

<210> SEQ ID NO 48
<211> LENGTH: 10
<212> TYPE: DNA
```

```
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddC

<400> SEQUENCE: 48
ctagagtagc                                                           10

<210> SEQ ID NO 49
<211> LENGTH: 10
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (3)..(9)
<223> OTHER INFORMATION: UMI
<220> FEATURE:
<221> NAME/KEY: misc_feature
<222> LOCATION: (10)..(10)
<223> OTHER INFORMATION: ddG

<400> SEQUENCE: 49
ctatccagag                                                           10

<210> SEQ ID NO 50
<211> LENGTH: 33
<212> TYPE: DNA
<213> ORGANISM: Artificial Sequence
<220> FEATURE:
<223> OTHER INFORMATION: synthetic nucleic acid

<400> SEQUENCE: 50
acactctttc cctacacgac gctcttccga tct                                 33

<210> SEQ ID NO 51
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 51
caagcagaag acggcatacg agatctgatc gtgtgactgg agttcagacg tgt           53

<210> SEQ ID NO 52
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 52
caagcagaag acggcatacg agatactctc gagtgactgg agttcagacg tgt           53
```

<210> SEQ ID NO 53
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 53
caagcagaag acggcatacg agattgagct aggtgactgg agttcagacg tgt        53

<210> SEQ ID NO 54
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 54
caagcagaag acggcatacg agatgagacg atgtgactgg agttcagacg tgt        53

<210> SEQ ID NO 55
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 55
caagcagaag acggcatacg agatcttgtc gagtgactgg agttcagacg tgt        53

<210> SEQ ID NO 56
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 56
caagcagaag acggcatacg agatttccaa gggtgactgg agttcagacg tgt        53

<210> SEQ ID NO 57
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 57

-continued caagcagaag acggcatacg agatcgcatg atgtgactgg agttcagacg tgt          53

<210> SEQ ID NO 58
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 58
caagcagaag acggcatacg agatacggaa cagtgactgg agttcagacg tgt          53

<210> SEQ ID NO 59
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 59
caagcagaag acggcatacg agatcggcta atgtgactgg agttcagacg tgt          53

<210> SEQ ID NO 60
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 60
caagcagaag acggcatacg agatatcgat cggtgactgg agttcagacg tgt          53

<210> SEQ ID NO 61
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 61
caagcagaag acggcatacg agatgcaaga tcgtgactgg agttcagacg tgt          53

<210> SEQ ID NO 62
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 62
caagcagaag acggcatacg agatgctatc ctgtgactgg agttcagacg tgt         53

<210> SEQ ID NO 63
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 63
caagcagaag acggcatacg agattacgct acgtgactgg agttcagacg tgt         53

<210> SEQ ID NO 64
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 64
caagcagaag acggcatacg agattggact ctgtgactgg agttcagacg tgt         53

<210> SEQ ID NO 65
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 65
caagcagaag acggcatacg agatagagta gcgtgactgg agttcagacg tgt         53

<210> SEQ ID NO 66
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 66
caagcagaag acggcatacg agatatccag aggtgactgg agttcagacg tgt         53

<210> SEQ ID NO 67
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 67
caagcagaag acggcatacg agatgacgat ctgtgactgg agttcagacg tgt    53

<210> SEQ ID NO 68
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 68
caagcagaag acggcatacg agataactga gcgtgactgg agttcagacg tgt    53

<210> SEQ ID NO 69
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 69
caagcagaag acggcatacg agatcttagg acgtgactgg agttcagacg tgt    53

<210> SEQ ID NO 70
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 70
caagcagaag acggcatacg agatgtgcca tagtgactgg agttcagacg tgt    53

<210> SEQ ID NO 71
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 71
caagcagaag acggcatacg agatgaatcc gagtgactgg agttcagacg tgt    53

<210> SEQ ID NO 72
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 72
caagcagaag acggcatacg agattcgctg ttgtgactgg agttcagacg tgt       53

<210> SEQ ID NO 73
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 73
caagcagaag acggcatacg agatttcgtt gggtgactgg agttcagacg tgt       53

<210> SEQ ID NO 74
<211> LENGTH: 53
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (25)..(32)
<223> OTHER INFORMATION: sample barcode

<400> SEQUENCE: 74
caagcagaag acggcatacg agataagcac tggtgactgg agttcagacg tgt       53

<210> SEQ ID NO 75
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 75
aatgatacgg cgaccaccga gatctacacc tgatcgtaca ctctttccct acacgac   57

<210> SEQ ID NO 76
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 76
aatgatacgg cgaccaccga gatctacaca ctctcgaaca ctctttccct acacgac   57

<210> SEQ ID NO 77
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)

<223> OTHER INFORMATION: sample barcode

<400> SEQUENCE: 77
aatgatacgg cgaccaccga gatctacact gagctagaca ctctttccct acacgac     57

<210> SEQ ID NO 78
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 78
aatgatacgg cgaccaccga gatctacacg agacgataca ctctttccct acacgac     57

<210> SEQ ID NO 79
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 79
aatgatacgg cgaccaccga gatctacacc ttgtcgaaca ctctttccct acacgac     57

<210> SEQ ID NO 80
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 80
aatgatacgg cgaccaccga gatctacact tccaaggaca ctctttccct acacgac     57

<210> SEQ ID NO 81
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 81
aatgatacgg cgaccaccga gatctacacc gcatgataca ctctttccct acacgac     57

<210> SEQ ID NO 82
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 82
aatgatacgg cgaccaccga gatctacaca cggaacaaca ctctttccct acacgac        57

<210> SEQ ID NO 83
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 83
aatgatacgg cgaccaccga gatctacacc ggctaataca ctctttccct acacgac        57

<210> SEQ ID NO 84
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 84
aatgatacgg cgaccaccga gatctacaca tcgatcgaca ctctttccct acacgac        57

<210> SEQ ID NO 85
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 85
aatgatacgg cgaccaccga gatctacacg caagatcaca ctctttccct acacgac        57

<210> SEQ ID NO 86
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 86
aatgatacgg cgaccaccga gatctacacg ctatcctaca ctctttccct acacgac        57

<210> SEQ ID NO 87
<211> LENGTH: 57
<212> TYPE: DNA
<213> ORGANISM: Artificial Sequence
<220> FEATURE:
<223> OTHER INFORMATION: synthetic nucleic acid
<220> FEATURE:

```
<221> NAME/KEY: misc_feature
<222> LOCATION: (30)..(37)
<223> OTHER INFORMATION: sample barcode

<400> SEQUENCE: 87
aatgatacgg cgaccaccga gatctacact acgctacaca ctctttccct acacgac    57

<210> SEQ ID NO 88
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 88
aatgatacgg cgaccaccga gatctacact ggactctaca ctctttccct acacgac    57

<210> SEQ ID NO 89
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 89
aatgatacgg cgaccaccga gatctacaca gagtagcaca ctctttccct acacgac    57

<210> SEQ ID NO 90
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 90
aatgatacgg cgaccaccga gatctacaca tccagagaca ctctttccct acacgac    57

<210> SEQ ID NO 91
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 91
aatgatacgg cgaccaccga gatctacacg acgatctaca ctctttccct acacgac    57

<210> SEQ ID NO 92
<211> LENGTH: 57
<212> TYPE: DNA
<213> ORGANISM: Artificial Sequence
<220> FEATURE:
<223> OTHER INFORMATION: synthetic nucleic acid
```

<220> FEATURE:
<221> NAME/KEY: misc_feature
<222> LOCATION: (30)..(37)
<223> OTHER INFORMATION: sample barcode

<400> SEQUENCE: 92
aatgatacgg cgaccaccga gatctacaca actgagcaca ctctttccct acacgac    57

<210> SEQ ID NO 93
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 93
aatgatacgg cgaccaccga gatctacacc ttaggacaca ctctttccct acacgac    57

<210> SEQ ID NO 94
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 94
aatgatacgg cgaccaccga gatctacacg tgccataaca ctctttccct acacgac    57

<210> SEQ ID NO 95
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 95
aatgatacgg cgaccaccga gatctacacg aatccgaaca ctctttccct acacgac    57

<210> SEQ ID NO 96
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 96
aatgatacgg cgaccaccga gatctacact cgctgttaca ctctttccct acacgac    57

<210> SEQ ID NO 97
<211> LENGTH: 57
<212> TYPE: DNA
<213> ORGANISM: Artificial Sequence
<220> FEATURE:

```
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 97
aatgatacgg cgaccaccga gatctacact tcgttggaca ctctttccct acacgac      57

<210> SEQ ID NO 98
<211> LENGTH: 57
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (30)..(37)
<223> OTHER INFORMATION: sample barcode

<400> SEQUENCE: 98
aatgatacgg cgaccaccga gatctacaca agcactgaca ctctttccct acacgac      57
```